US010648033B2

(12) United States Patent
Khatri et al.

(10) Patent No.: US 10,648,033 B2
(45) Date of Patent: *May 12, 2020

(54) BIOMARKERS FOR USE IN PROGNOSIS OF MORTALITY IN CRITICALLY ILL PATIENTS

(71) Applicant: The Board of Trustees of the Leland Stanford Junior University, Stanford, CA (US)

(72) Inventors: Purvesh Khatri, Menlo Park, CA (US); Timothy E. Sweeney, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,358

(22) Filed: May 20, 2019

(65) Prior Publication Data

US 2019/0300959 A1 Oct. 3, 2019

Related U.S. Application Data

(63) Continuation of application No. 15/553,152, filed as application No. PCT/US2017/029468 on Apr. 25, 2017, now Pat. No. 10,344,332.

(60) Provisional application No. 62/354,789, filed on Jun. 26, 2016.

(51) Int. Cl.
*C12Q 1/68* (2018.01)
*C12Q 1/6883* (2018.01)
*G16B 25/00* (2019.01)
*C40B 40/06* (2006.01)
*C40B 40/08* (2006.01)
*G01N 33/50* (2006.01)
*G01N 33/68* (2006.01)
*G16B 25/10* (2019.01)

(52) U.S. Cl.
CPC ............ *C12Q 1/6883* (2013.01); *C40B 40/06* (2013.01); *C40B 40/08* (2013.01); *G01N 33/50* (2013.01); *G01N 33/6893* (2013.01); *G16B 25/00* (2019.02); *G16B 25/10* (2019.02); *C12Q 2537/165* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 10,344,332 B2 * | 7/2019 | Khatri | ............... C40B 40/06 |
| 2005/0196817 A1 | 9/2005 | Kingsmore et al. | |
| 2012/0034214 A1 | 2/2012 | Ho | |
| 2016/0055295 A1 | 2/2016 | Brandon et al. | |

OTHER PUBLICATIONS

Nelson et al., "Biomarkers for Sepsis: A Review with Special Attention to India", Hindawi Publishing Corporation, BioMed Research International, 2014, vol. 2014, Article ID 264351, 11 pages.
Handbook of Chemistry and Physics, 49th Edition, 1968, Weast (ed.), The Chemical Rubber Co., p. A-245.
Affymetrix, "GeneChip Human Genome U133 Set", Affymetrix, 2003, XP002232760, http://www.affymetrix.com/ support/technical/datasheets/hgu133_datasheet.pdf.
Parnell et al., "Identifying Key Regulatory Genes in the Whole Blood of Septic Patients to Monitor Underlying Immune Dysfunctions", Shock Society, 2013, 40(3):166-174.
Sweeney et al., Risk stratification and prognosis in sepsis: what have we learned from microarrays?', Clinics in Chest Medicine, 2016, 37(2):209-218.
Sweeney et al., "Mortality Prediction in sepsis via gene expression analysis: a community approach", bioRxiv, 2016, XP055653359, https://www.biorxiv.org/content/10.1101/095489v1.full.pdf.
Tsalik et al., "An integrated transcriptome and expressed variant analysis of sepsis survival and death", Genome Medicine, 2014, 6(11):111.

* cited by examiner

*Primary Examiner* — James Martinell
(74) *Attorney, Agent, or Firm* — James S. Keddie; Bozicevic, Field & Francis LLP

(57) ABSTRACT

Biomarkers and methods of using them for aiding diagnosis, prognosis, and treatment of critically ill patients are disclosed. In particular, the invention relates to the use of biomarkers for prognosis of mortality in critically ill patients with sepsis, severe trauma, or burns.

11 Claims, 23 Drawing Sheets

BIOMARKERS FOR USE IN PROGNOSIS OF MORTALITY IN CRITICALLY ILL PATIENTS

CROSS-REFERENCING

This application is a continuation of U.S. application Ser. No. 15/553,152, filed on Aug. 23, 2017, which is a § 371 national phase of International Application No. PCT/US2017/029468, filed on Apr. 25, 2017, which claims the benefit of U.S. Provisional Application Ser. No. 62/354,789, filed on Jun. 26, 2016, which applications are incorporated by reference herein.

STATEMENT REGARDING FEDERALLY SPONSORED RESEARCH OR DEVELOPMENT

This invention was made with Government support under contracts AI057229, AI089859, AI109662, and AI117925 awarded by the National Institutes of Health. The Government has certain rights in the invention.

TECHNICAL FIELD

The present invention pertains generally to methods for prognosis of mortality risk in critically ill patients. In particular, the invention relates to the use of biomarkers that can be used for prognosis of mortality risk in critically ill patients with sepsis, severe trauma, or burns.

BACKGROUND

Sepsis, newly defined as organ failure caused by systemic response to infection[1], contributes to half of all in-hospital deaths in the US, and is also the number one overall cost to the US healthcare system.[2,3] Although sepsis outcomes have improved over the last decade with improvement in standardized sepsis care, mortality rates remain high (10-35%)[4]. Sepsis treatment still consists of source control, antibiotics, and supportive care. Despite dozens of clinical trials for immune-modulating intervention, no treatments specific for sepsis have been successfully brought to market[5]. Two consensus papers have argued that the failure of clinical trials is due to the massive patient heterogeneity in the sepsis syndrome, and our lack of tools for accurate molecular profiling[5,6]. Current tools, mainly clinical severity scores such as APACHE and SOFA, and the blood lactate level, are not readouts of the underlying inflammation in sepsis, but rather a crude look at the global level of patient illness.

Several groups have hypothesized that transcriptomic (genome-wide expression) profiling of the immune system via analysis of the whole blood may be an effective way to stratify sepsis patients. Important insights from these studies include overexpression of neutrophils proteases, a collapse in adaptive immunity, and an overall profound immune dysregulation in sepsis[7-12]. Some immune profiling techniques have been validated prospectively to show outcomes differences[13,14], but no clinical tools have yet been translated into clinical practice. Still, most of these studies have been deposited in public databases for further re-analysis and re-use.

Thus, new molecular profiling tools are needed, both for improved patient care and resource stratification, but also as research tools for better clinical trials in sepsis.

SUMMARY

The invention relates to the use of biomarkers for aiding diagnosis, prognosis, and treatment of critically ill patients. In particular, the invention relates to the use of biomarkers for prognosis of mortality in critically ill patients with sepsis, severe trauma, or burns.

Biomarkers that can be used in the practice of the invention include polynucleotides comprising nucleotide sequences from genes or RNA transcripts of genes, including but not limited to, DEFA4, CD163, PER1, RGS1, HIF1A, SEPP1, C11orf74, CIT, LY86, TST, OR52R1, and KCNJ2.

In certain embodiments, a panel of biomarkers is used for prognosis of mortality. Biomarker panels of any size can be used in the practice of the invention. Biomarker panels for prognosis of mortality typically comprise at least 3 biomarkers and up to 30 biomarkers, including any number of biomarkers in between, such as 3, 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 3, at least 4, or at least 5, or at least 6, or at least 7, or at least 8, or at least 9, or at least 10, or at least 11 or more biomarkers. Although smaller biomarker panels are usually more economical, larger biomarker panels (i.e., greater than 30 biomarkers) have the advantage of providing more detailed information and can also be used in the practice of the invention.

In one embodiment, the biomarker panel comprises a plurality of biomarkers for prognosis of mortality, wherein the plurality of biomarkers comprises one or more polynucleotides comprising a nucleotide sequence from a gene or an RNA transcript of a gene selected from the group consisting of DEFA4, CD163, PER1, RGS1, HIF1A, SEPP1, C11orf74, CIT, LY86, TST, OR52R1, and KCNJ2. In one embodiment the biomarker panel comprises a DEFA4 polynucleotide, a CD163 polynucleotide, a PER1 polynucleotide, a RGS1 polynucleotide, an HIF1A polynucleotide, a SEPP1 polynucleotide, a C11orf74 polynucleotide, a CIT polynucleotide, LY86 polynucleotide, a TST polynucleotide, an OR52R1 polynucleotide, and a KCNJ2 polynucleotide.

In one aspect, the invention includes a method of determining mortality risk and treating a patient suspected of having a life-threatening condition. The method comprises a) obtaining a biological sample from the patient; b) measuring levels of expression of DEFA4, CD163, PER1, RGS1, HIF1A, SEPP1, C11orf74, CIT, LY86, TST, OR52R1, and KCNJ2 biomarkers in the biological sample; and c) analyzing the levels of expression of each biomarker in conjunction with respective reference value ranges for the biomarkers, wherein increased levels of expression of the DEFA4, CD163, PER1, RGS1, HIF1A, SEPP1, C11orf74, and CIT biomarkers and decreased levels of expression of the LY86, TST, OR52R1, and KCNJ2 biomarkers compared to the reference value ranges for the biomarkers for a control subject indicate that the patient is at high risk of mortality within 30 days; and d) administering intensive care unit (ICU) treatment to the patient if the patient is at high risk of mortality within 30 days. In certain embodiments, the life-threatening condition is sepsis, trauma, or a burn.

The reference value ranges can represent the levels of one or more biomarkers found in one or more samples of one or more subjects without a critical illness (e.g., healthy subject or subject without infection or injury). Alternatively, the reference values can represent the levels of one or more biomarkers found in one or more samples of one or more subjects with a critical illness (e.g., sepsis/infection, severe trauma or burn). In certain embodiments, the levels of the biomarkers are compared to time-matched reference values ranges for non-infected and infected/septic subjects or injured (e.g., severe trauma or burn) and non-injured subjects.

In certain embodiments, the method is performed prior to or upon admission to an intensive care unit. The method may be performed within 14 days of admission to a hospital, such as within 24 hours, 48 hours, 3 days, 4, days, 5, days, 6 days, 7 days, 8 days, 9 days, 10 days, 11 days, 12 days, 13 days, or 14 days. In another embodiment, the method is performed 3 to 7 days after diagnosis of sepsis in the patient. In another embodiment, the method is performed 3 to 14 days after burn of the patient. In a further embodiment, the method is performed 3 to 14 days after injury of the patient.

The biological sample may comprise, for example, blood, buffy coat, band cells, or metamyelocytes.

Biomarker polynucleotides (e.g., coding transcripts) can be detected, for example, by microarray analysis, polymerase chain reaction (PCR), reverse transcriptase polymerase chain reaction (RT-PCR), Northern blot, or serial analysis of gene expression (SAGE).

In another aspect, the invention includes a method of determining a mortality gene score for a subject suspected of having a life-threatening condition, the method comprising: a) collecting a biological sample from the subject; b) measuring the levels of a plurality of biomarkers, described herein, in the biological sample; and c) determining the mortality gene score for the biomarkers by subtracting the geometric mean of the expression levels of all biomarkers that are underexpressed compared to control reference values for the biomarkers from the geometric mean of the expression levels of all biomarkers that are overexpressed compared to control reference values for the biomarkers, and multiplying the difference by the ratio of the number of biomarkers that are overexpressed to the number of biomarkers that are underexpressed compared to control reference values for the biomarkers.

In another embodiment, the method further comprises calculating a mortality gene score for the patient based on the levels of the biomarkers, wherein a higher mortality gene score for the patient compared to a control subject indicates that the patient is at high risk of mortality within 30 days.

In certain embodiments, the mortality gene score is calculated from the expression levels of a plurality of biomarkers comprising one or more polynucleotides comprising a nucleotide sequence from a gene or an RNA transcript of a gene selected from the group consisting of DEFA4, CD163, PER1, RGS1, HIF1A, SEPP1, C11orf74, CIT, LY86, TST, OR52R1, and KCNJ2. In one embodiment, the plurality of biomarkers comprises a DEFA4 polynucleotide, a CD163 polynucleotide, a PER1 polynucleotide, a RGS1 polynucleotide, an HIF1A polynucleotide, a SEPP1 polynucleotide, a C11orf74 polynucleotide, a CIT polynucleotide, LY86 polynucleotide, a TST polynucleotide, an OR52R1 polynucleotide, and a KCNJ2 polynucleotide.

In another embodiment, the invention includes a method of determining mortality risk and treating a patient having sepsis, the method comprising: a) obtaining a biological sample from the patient; b) measuring levels of expression of DEFA4, CD163, PER1, RGS1, HIF1A, SEPP1, C11orf74, CIT, LY86, TST, OR52R1, and KCNJ2 biomarkers in the biological sample; and c) calculating a mortality gene score for the patient based on the levels of the biomarkers, wherein a higher mortality gene score for the patient compared to a control subject indicates that the patient is at high risk of mortality within 30 days; and d) administering intensive care unit treatment to the patient if the patient is at high risk of mortality within 30 days.

In other embodiments, the invention includes a method of diagnosing and treating a patient having an infection, the method comprising: a) obtaining a biological sample from the patient; b) measuring levels of expression of DEFA4, CD163, PER1, RGS1, HIF1A, SEPP1, C11orf74, CIT, LY86, TST, OR52R1, and KCNJ2 biomarkers in the biological sample, wherein increased levels of expression of the DEFA4, CD163, PER1, RGS1, HIF1A, SEPP1, C11orf74, and CIT biomarkers and decreased levels of expression of the LY86, TST, OR52R1, and KCNJ2 biomarkers compared to the reference value ranges for the biomarkers for a control subject indicate that the patient has sepsis; and c) administering a sepsis treatment comprising antimicrobial therapy, supportive care, or an immune-modulating therapy if the patient is diagnosed with sepsis. In another embodiment, the method further comprises calculating a mortality gene score for the patient based on the levels of the biomarkers, wherein a higher mortality gene score for the patient compared to a control subject indicates that the patient is at high risk of mortality within 30 days; and administering intensive care unit treatment to the patient if the patient is at high risk of mortality within 30 days.

In another aspect, the invention includes a method of treating a patient suspected of having a life-threatening condition, the method comprising: a) receiving information regarding the prognosis of the patient according to a method described herein; and b) administering intensive care unit treatment to the patient if the patient is at high risk of mortality within 30 days.

In certain embodiments, patient data is analyzed by one or more methods including, but not limited to, multivariate linear discriminant analysis (LDA), receiver operating characteristic (ROC) analysis, principal component analysis (PCA), ensemble data mining methods, cell specific significance analysis of microarrays (csSAM), and multi-dimensional protein identification technology (MUDPIT) analysis.

In another aspect, the invention includes a kit for prognosis of mortality in a subject. The kit may include a container for holding a biological sample isolated from a human subject suspected of having a life-threatening condition, at least one agent that specifically detects a biomarker; and printed instructions for reacting the agent with the biological sample or a portion of the biological sample to detect the presence or amount of at least one biomarker in the biological sample. The agents may be packaged in separate containers. The kit may further comprise one or more control reference samples and reagents for performing PCR or microarray analysis for detection of biomarkers as described herein.

In certain embodiments, the kit includes agents for detecting polynucleotides of a biomarker panel comprising a plurality of biomarkers for prognosis of mortality, wherein one or more biomarkers are selected from the group consisting of a DEFA4 polynucleotide, a CD163 polynucleotide, a PER1 polynucleotide, a RGS1 polynucleotide, an HIF1A polynucleotide, a SEPP1 polynucleotide, a C11orf74 polynucleotide, a CIT polynucleotide, LY86 polynucleotide, a TST polynucleotide, an OR52R1 polynucleotide, and a KCNJ2 polynucleotide. In one embodiment, the kit includes agents for detecting biomarkers of a biomarker panel comprising a DEFA4 polynucleotide, a CD163 polynucleotide, a PER1 polynucleotide, a RGS1 polynucleotide, an HIF1A polynucleotide, a SEPP1 polynucleotide, a C11orf74 polynucleotide, a CIT polynucleotide, LY86 polynucleotide, a TST polynucleotide, an OR52R1 polynucleotide, and a KCNJ2 polynucleotide.

In certain embodiments, the kit comprises a microarray for analysis of a plurality of biomarker polynucleotides. In one embodiment, the kit comprises a microarray comprising an oligonucleotide that hybridizes to a DEFA4 polynucleotide, an oligonucleotide that hybridizes to a CD163 polynucleotide, an oligonucleotide that hybridizes to a PER1 polynucleotide, an oligonucleotide that hybridizes to a RGS1 polynucleotide, an oligonucleotide that hybridizes to an HIF1A polynucleotide, an oligonucleotide that hybridizes to a SEPP1 polynucleotide, an oligonucleotide that hybridizes to a C11orf74 polynucleotide, an oligonucleotide that hybridizes to a CIT polynucleotide, an oligonucleotide that hybridizes to a LY86 polynucleotide, an oligonucleotide that hybridizes to a TST polynucleotide, an oligonucleotide that hybridizes to an OR52R1 polynucleotide, and an oligonucleotide that hybridizes to a KCNJ2 polynucleotide.

In another aspect, the invention includes a diagnostic system comprising a storage component (i.e., memory) for storing data, wherein the storage component has instructions for determining the diagnosis of the subject stored therein; a computer processor for processing data, wherein the computer processor is coupled to the storage component and configured to execute the instructions stored in the storage component in order to receive patient data and analyze patient data according to an algorithm; and a display component for displaying information regarding the diagnosis of the patient. The storage component may include instructions for determining the mortality risk of the subject, as described herein (see Examples 1). Additionally, the storage component may further include instructions for calculating a mortality gene score.

In certain embodiments, the invention includes a computer implemented method for determining mortality risk of a patient suspected of having a life-threatening condition, the computer performing steps comprising: a) receiving inputted patient data comprising values for levels of expression of DEFA4, CD163, PER1, RGS1, HIF1A, SEPP1, C11orf74, CIT, LY86, TST, OR52R1, and KCNJ2 biomarkers in a biological sample from the patient; b) analyzing the level of each biomarker and comparing with respective reference value ranges for each biomarker; c) calculating a mortality gene score for the patient based on the levels of the biomarkers, wherein a higher mortality gene score for the patient compared to a control subject indicates that the patient is at high risk of mortality within 30 days; and d) displaying information regarding the mortality risk of the patient.

In certain embodiments, the inputted patient data comprises values for the levels of at least 12 biomarkers in a biological sample from the patient. For example, the inputted patient data may comprises values for the levels of a DEFA4 polynucleotide, a CD163 polynucleotide, a PER1 polynucleotide, a RGS1 polynucleotide, an HIF1A polynucleotide, a SEPP1 polynucleotide, a C11orf74 polynucleotide, a CIT polynucleotide, LY86 polynucleotide, a TST polynucleotide, an OR52R1 polynucleotide, and a KCNJ2 polynucleotide.

In another embodiment, the invention includes a composition comprising a plurality of in vitro complexes, wherein the plurality of in vitro complexes comprise labeled probes hybridized to nucleic acids comprising biomarker DEFA4, CD163, PER1, RGS1, HIF1A, SEPP1, C11orf74, CIT, LY86, TST, OR52R1, and KCNJ2 gene sequences, said labeled probes hybridized to the biomarker gene sequences, or their complements, wherein said nucleic acids are extracted from a patient who has a life-threatening condition (e.g., sepsis, severe trauma, or burn) or are amplification products of the nucleic acids extracted from the patient who has a life-threatening condition. Probes may be detectably labeled with any type of label, including, but not limited to, a fluorescent label, bioluminescent label, chemiluminescent label, colorimetric label, or isotopic label (e.g., stable trace isotope or radioactive isotope). In certain embodiments, the composition is in a detection device (i.e., device capable of detecting labeled probe).

These and other embodiments of the subject invention will readily occur to those of skill in the art in view of the disclosure herein.

BRIEF DESCRIPTION OF THE FIGURES

FIG. 10A shows ROC plots of mortality prediction broken into bins of time since admission. FIG. 10B shows individual patient trajectories, separated by survivor status.

FIG. 11A shows ROC plots of mortality prediction broken into bins of time since admission. FIG. 11B shows individual patient trajectories, separated by survivor status.

FIG. 12A shows individual patient trajectories of the 12-gene score, separated by survivor status. FIG. 12B shows individual patient trajectories of the MODS score, separated by survivor status.

FIG. 13A shows sepsis patients in Day6-Day10 time window at time of diagnosis (N=12 survivors, 1 non-TBI death). FIG. 13B shows all patients broken into bins based on day since admission; shown is all-cause mortality prediction. N=179 survivors and 8 non-survivors at Day 0; later timepoints show the same patients.

FIG. 14A shows individual patient trajectories of the 12-gene score, separated by survivor status. FIG. 14B shows individual patient trajectories of the Denver score, separated by survivor status.

FIG. 15A shows sepsis patients at Day1-Day3 (N=63 survivors, 3 non-survivors) and Day3-Day7 (N=15 survivors, 5 non-survivors) time windows at time of diagnosis. FIG. 15B shows all patients broken into bins based on day since admission; shown is all-cause mortality prediction. N=212 survivors and 22 non-survivors at Day 0; later timepoints show the same patients.

DETAILED DESCRIPTION

Figure 1:
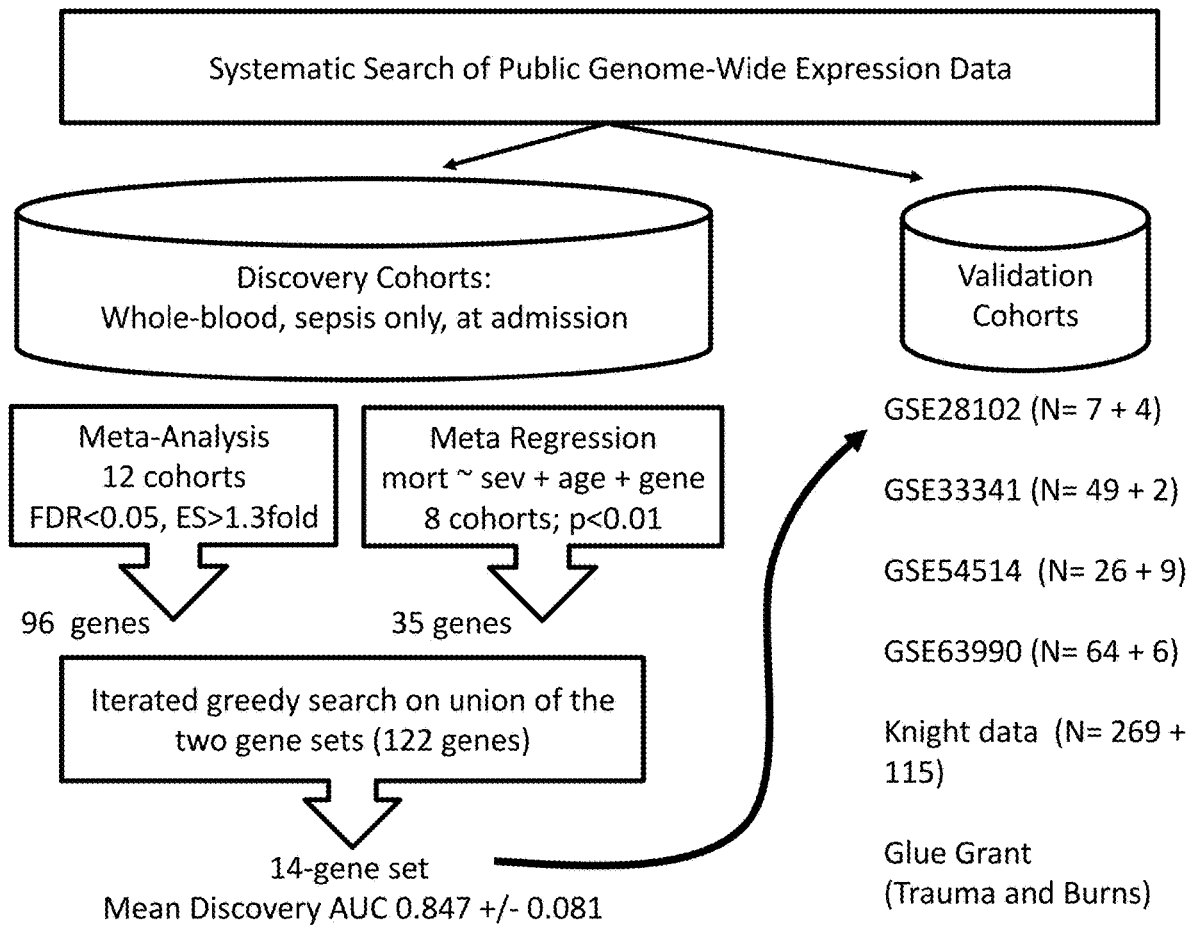
FIG. 1 shows the overall study schematic.
Figure 2:
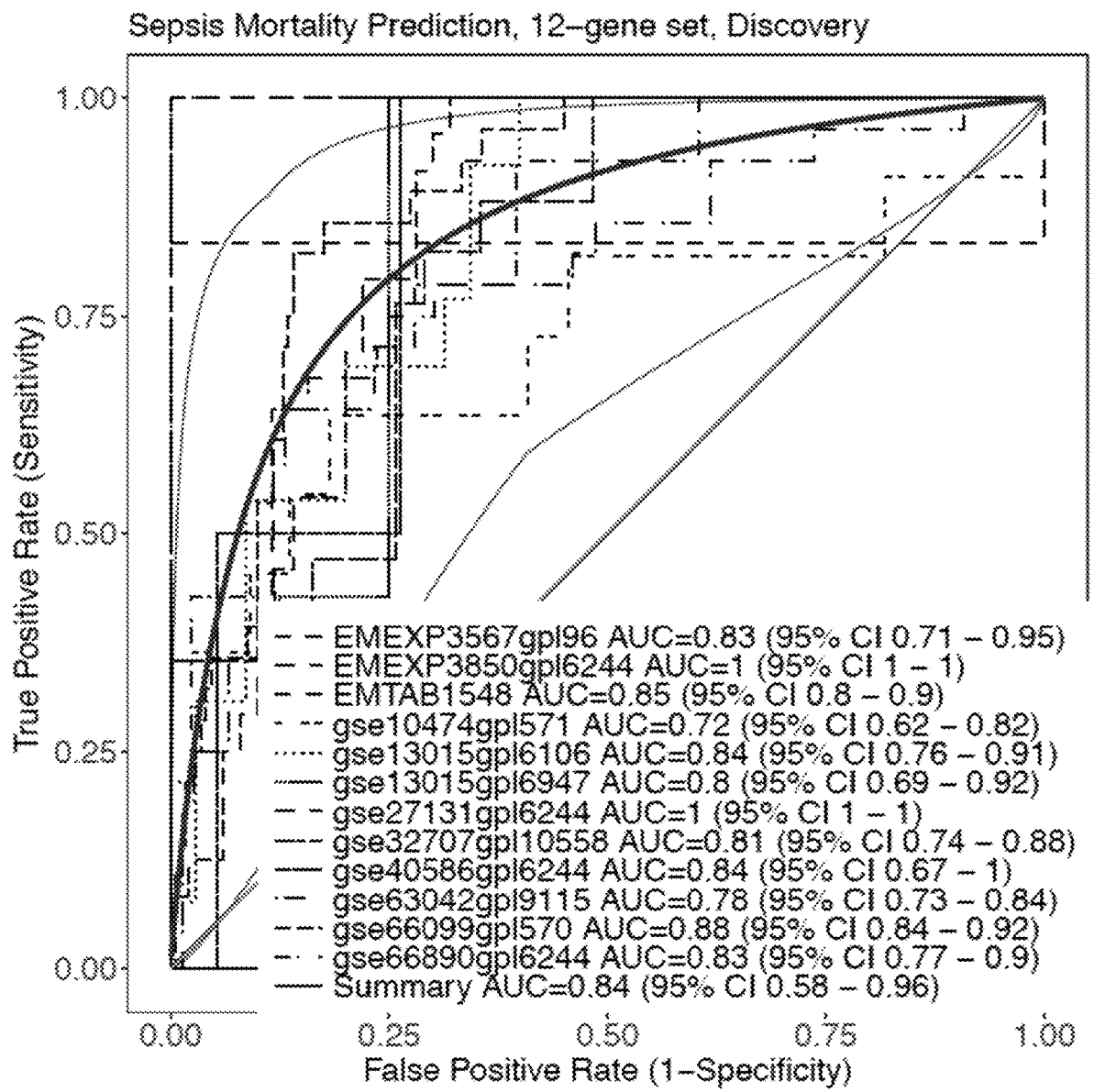
FIG. 2 shows summary ROC curves from discovery datasets. Shown is the prognostic power of the 12-gene set for prediction of mortality in septic patients at admission.
Figure 3:
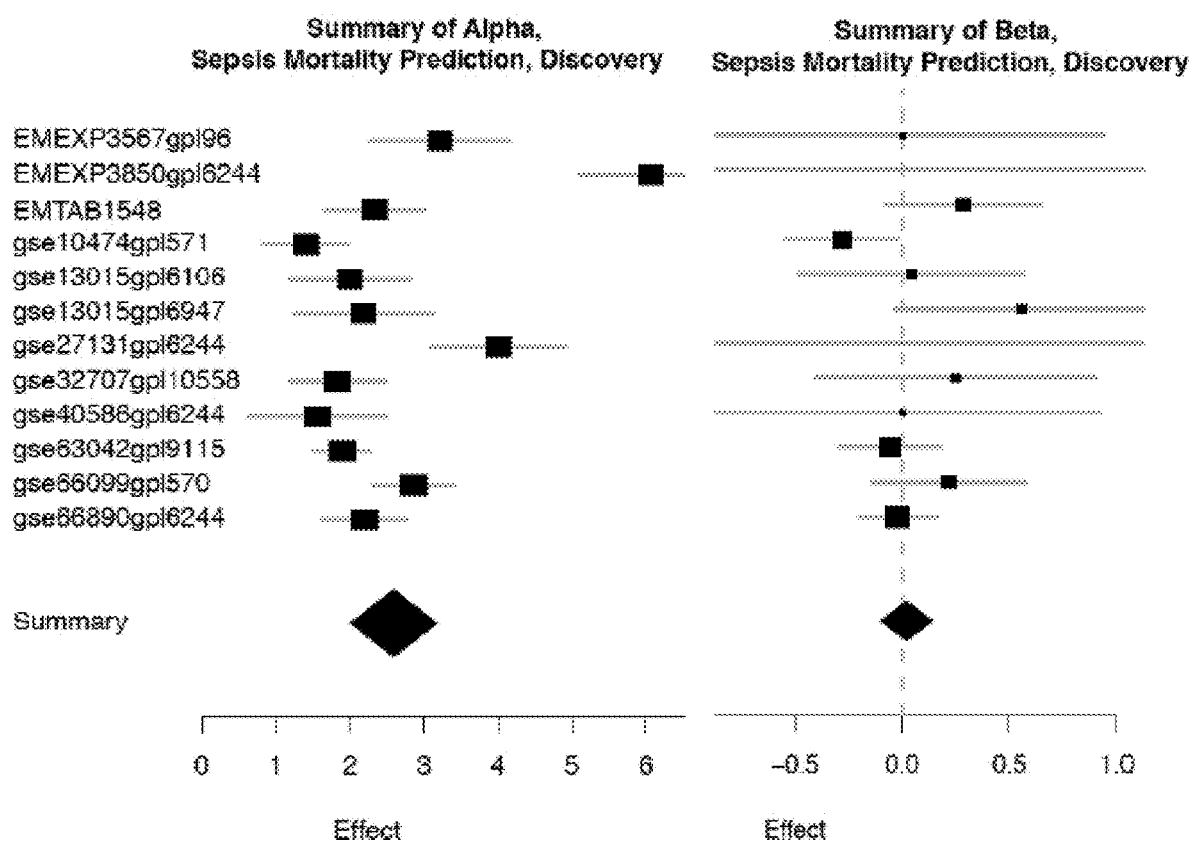
FIG. 3 shows Forest plots of the alpha and beta parameters for the summary ROC curve in the discovery datasets from FIG. 2.
Figure 4:
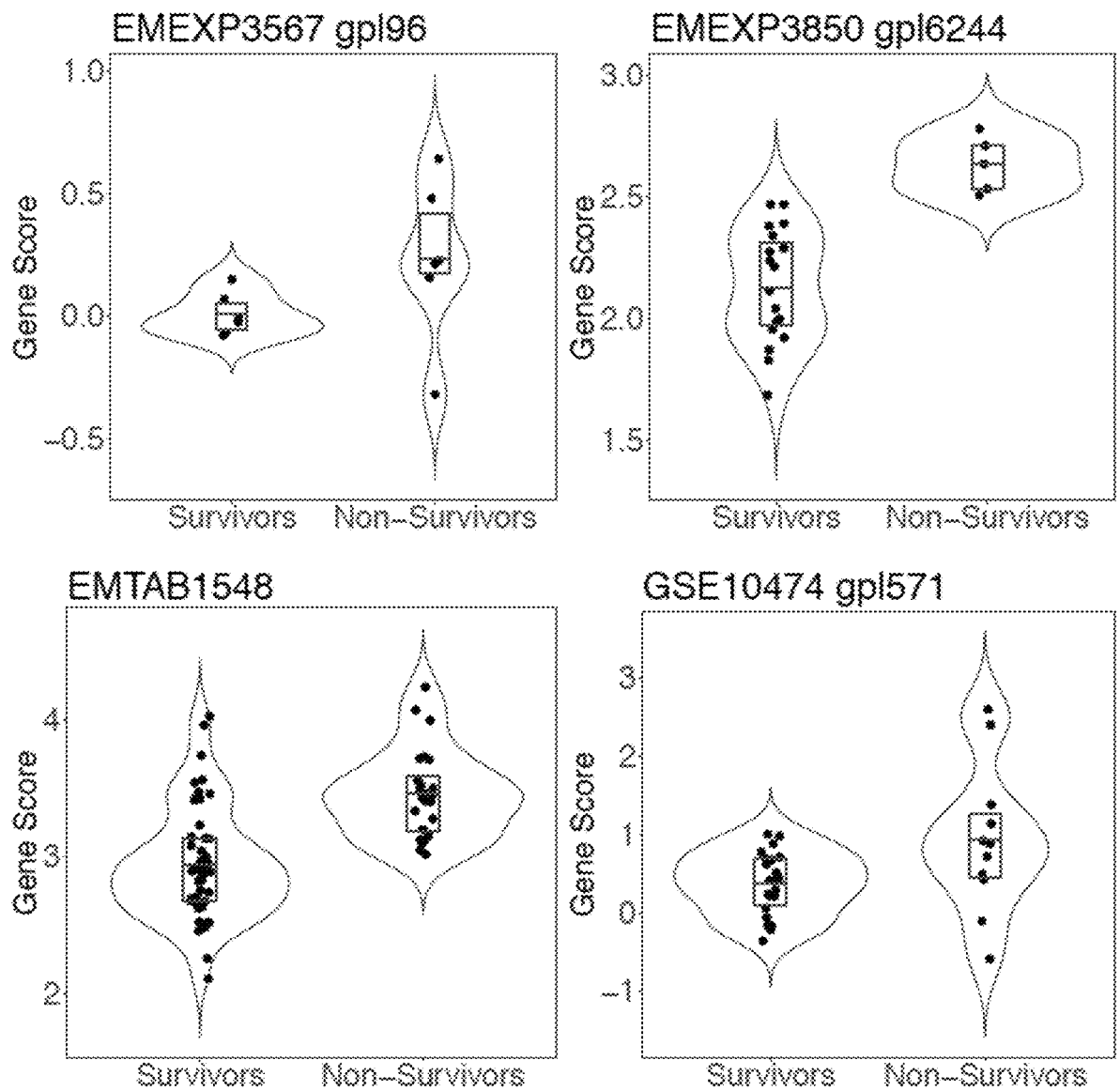
FIGS. 4-6 show violin plots of the 12-gene scores for individual patients in the discovery cohorts, separate by survivor status. Inner bars show mean and inter-quartile range.
Figure 5:
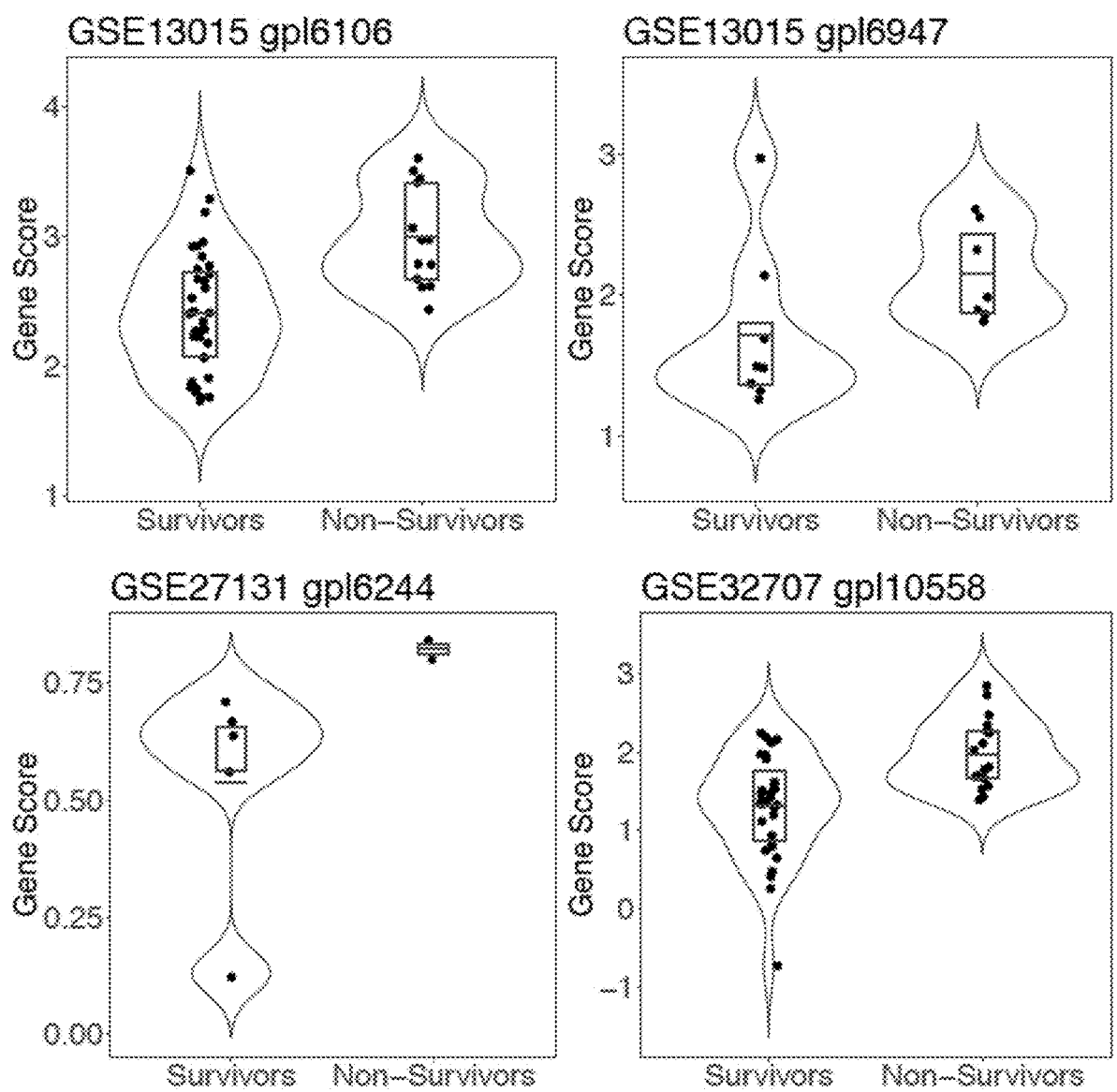
Figure 6:
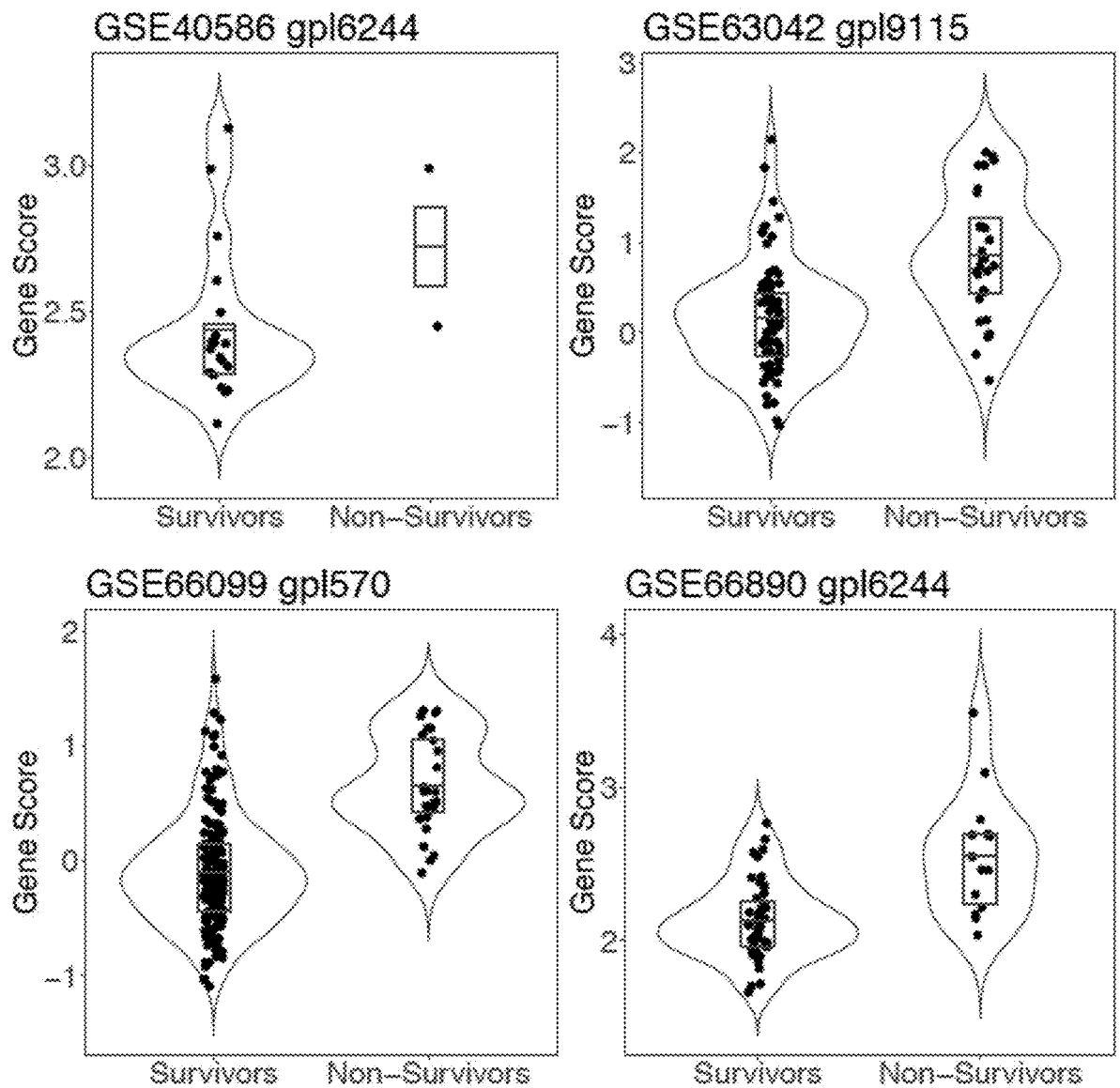

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., J. R. Brown *Sepsis: Symptoms, Diagnosis and Treatment* (Public Health in the 21st Century Series, Nova Science Publishers, Inc., 2013); *Sepsis and Non-infectious Systemic Inflammation: From Biology to Critical Care* (J. Cavaillon, C. Adrie eds., Wiley-Blackwell, 2008); *Sepsis: Diagnosis, Management and Health Outcomes* (Allergies and Infectious Diseases, N. Khardori ed., Nova Science Pub Inc., 2014); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3rd Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an," and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

The term "survival" means the time from a determination of mortality risk of a subject, using biomarkers as described herein, to the time of death.

The term "survivor" as used herein refers to a subject who will live for at least 30 more days.

The term "non-survivor" as used herein refers to a subject who will die within 30 days.

A "biomarker" in the context of the present invention refers to a biological compound, such as a polynucleotide which is differentially expressed in a sample taken from a survivor as compared to a comparable sample taken from a non-survivor of a critical illness or condition (e.g., sepsis, severe trauma, or burn). The biomarker can be a nucleic acid, a fragment of a nucleic acid, a polynucleotide, or an oligonucleotide that can be detected and/or quantified. Biomarkers include polynucleotides comprising nucleotide sequences from genes or RNA transcripts of genes, including but not limited to, DEFA4, CD163, PER1, RGS1, HIF1A, SEPP1, C11orf74, CIT, LY86, TST, OR52R1, and KCNJ2.

The terms "polypeptide" and "protein" refer to a polymer of amino acid residues and are not limited to a minimum length. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation, hydroxylation, oxidation, and the like.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), and any other type of polynucleotide which is an N- or C-glycoside of a purine or pyrimidine base. There is no intended distinction in length between the terms "polynucleotide," "oligonucleotide," "nucleic acid" and "nucleic acid molecule," and these terms are used interchangeably.

The phrase "differentially expressed" refers to differences in the quantity and/or the frequency of a biomarker present in a sample taken from patients having a life-threatening condition (e.g., sepsis, severe trauma, or burn) at high risk of mortality within 30 days (i.e., non-survivor) as compared to a control subject at low risk of mortality within 30 days (i.e., survivor). For example, a biomarker can be a polynucleotide which is present at an elevated level or at a decreased level in samples of patients with sepsis compared to samples of control subjects. Alternatively, a biomarker can be a polynucleotide which is detected at a higher frequency or at a lower frequency in samples of patients at high risk of mortality within 30 days (i.e., non-survivors) compared to samples of control subjects. A biomarker can be differentially present in terms of quantity, frequency or both.

A polynucleotide is differentially expressed between two samples if the amount of the polynucleotide in one sample is statistically significantly different from the amount of the polynucleotide in the other sample. For example, a polynucleotide is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polynucleotide is differentially expressed in two sets of samples if the frequency of detecting the polynucleotide in samples of patients at high risk of mortality within 30 days (i.e., non-survivors) is statistically significantly higher or lower than in the control samples. For example, a polynucleotide is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

A "similarity value" is a number that represents the degree of similarity between two things being compared. For example, a similarity value may be a number that indicates the overall similarity between a patient's expression profile using specific phenotype-related biomarkers and reference value ranges for the biomarkers in one or more control samples or a reference expression profile (e.g., the similarity to a "survivor" expression profile or a "non-survivor" expression profile). The similarity value may be expressed as a similarity metric, such as a correlation coefficient, or may simply be expressed as the expression level difference, or the aggregate of the expression level differences, between levels of biomarkers in a patient sample and a control sample or reference expression profile.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; and primates.

As used herein, a "biological sample" refers to a sample of tissue, cells, or fluid isolated from a subject, including but not limited to, for example, blood, buffy coat, plasma, serum, blood cells (e.g., peripheral blood mononucleated cells (PBMCS), band cells, neutrophils, metamyelocytes, monocytes, or T cells), fecal matter, urine, bone marrow, bile, spinal fluid, lymph fluid, samples of the skin, external secretions of the skin, respiratory, intestinal, and genitourinary tracts, tears, saliva, milk, organs, biopsies and also samples of in vitro cell culture constituents, including, but not limited to, conditioned media resulting from the growth of cells and tissues in culture medium, e.g., recombinant cells, and cell components.

A "test amount" of a biomarker refers to an amount of a biomarker present in a sample being tested. A test amount can be either an absolute amount (e.g., µg/ml) or a relative amount (e.g., relative intensity of signals).

A "diagnostic amount" of a biomarker refers to an amount of a biomarker in a subject's sample that is consistent with a diagnosis of sepsis or prognosis of mortality. A diagnostic amount can be either an absolute amount (e.g., µg/ml) or a relative amount (e.g., relative intensity of signals).

A "control amount" of a biomarker can be any amount or a range of amount which is to be compared against a test amount of a biomarker. For example, a control amount of a biomarker can be the amount of a biomarker in a person without a life-threatening condition (e.g., person without sepsis, severe trauma, or burn), healthy person, or a survivor. A control amount can be either in absolute amount (e.g., µg/ml) or a relative amount (e.g., relative intensity of signals).

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

"Detectable moieties" or "detectable labels" contemplated for use in the invention include, but are not limited to, radioisotopes, fluorescent dyes such as fluorescein, phycoerythrin, Cy-3, Cy-5, allophycoyanin, DAPI, Texas Red, rhodamine, Oregon green, Lucifer yellow, and the like, green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding β-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Diagnosis" as used herein generally includes determination as to whether a subject is likely affected by a given disease, disorder or dysfunction. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

"Substantially purified" refers to nucleic acid molecules or proteins that are removed from their natural environment and are isolated or separated, and are at least about 60% free, preferably about 75% free, and most preferably about 90% free, from other components with which they are naturally associated.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The invention relates to the use of biomarkers either alone or in combination with clinical parameters for aiding diagnosis, prognosis, and treatment of critically ill patients. In particular, the inventors have discovered biomarkers whose expression profiles can be used for prognosis of mortality in critically ill patients with sepsis, severe trauma, or burns (see Example 1).

In order to further an understanding of the invention, a more detailed discussion is provided below regarding the identified biomarkers and methods of using them in diagnosis, prognosis, and treatment of critically ill patients.

A. Biomarkers

Biomarkers that can be used in the practice of the invention include polynucleotides comprising nucleotide sequences from genes or RNA transcripts of genes, including but not limited to, DEFA4, CD163, PER1, RGS1, HIF1A, SEPP1, C11orf74, CIT, LY86, TST, OR52R1, and KCNJ2. Differential expression of these biomarkers is associated with a high risk of mortality (within 30 days) and therefore expression profiles of these biomarkers are useful for prognosis of mortality in critically ill patients.

Accordingly, in one aspect, the invention provides a method of determining mortality risk of a subject, comprising measuring the level of a plurality of biomarkers in a biological sample derived from a subject suspected of having a life-threatening condition, and analyzing the levels of the biomarkers and comparing with respective reference value ranges for the biomarkers, wherein differential expression of one or more biomarkers in the biological sample compared to one or more biomarkers in a control sample indicates that the subject is at high risk of mortality within 30 days.

When analyzing the levels of biomarkers in a biological sample, the reference value ranges can represent the levels of one or more biomarkers found in one or more samples of one or more subjects without a critical illness (e.g., a survivor, healthy subject, or subject without infection or injury). Alternatively, the reference values can represent the levels of one or more biomarkers found in one or more samples of one or more subjects with a critical illness (e.g., a non-survivor, a subject with sepsis/infection, severe trauma, or burn). In certain embodiments, the levels of the biomarkers are compared to time-matched reference values ranges for non-infected and infected/septic subjects or injured (e.g., severe trauma or burn) and non-injured subjects.

The biological sample obtained from the subject to be diagnosed is typically whole blood, buffy coat, plasma, serum, or blood cells (e.g., peripheral blood mononucleated cells (PBMCS), band cells, metamyelocytes, neutrophils, monocytes, or T cells), but can be any sample from bodily fluids, tissue or cells that contain the expressed biomarkers. A "control" sample, as used herein, refers to a biological sample, such as a bodily fluid, tissue, or cells that are not diseased. That is, a control sample is obtained from a normal subject (e.g. an individual known to not have a life-threatening condition), a person who does not have sepsis, severe trauma, or burn, or a survivor. A biological sample can be obtained from a subject by conventional techniques. For example, blood can be obtained by venipuncture, and solid tissue samples can be obtained by surgical techniques according to methods well known in the art.

In certain embodiments, a panel of biomarkers is used for prognosis of mortality risk. Biomarker panels of any size can be used in the practice of the invention. Biomarker panels for prognosis of mortality typically comprise at least 3 biomarkers and up to 30 biomarkers, including any number of biomarkers in between, such as 3, 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 3, or at least 4, or at least 5, or at least 6, or at least 7, or at least 8, or at least 9, or at least 10, or at least 11 or more biomarkers. Although smaller biomarker panels are usually more economical, larger biomarker panels (i.e., greater than 30 biomarkers) have the advantage of providing more detailed information and can also be used in the practice of the invention.

In certain embodiments, the invention includes a panel of biomarkers for prognosis of mortality risk comprising one or more polynucleotides comprising a nucleotide sequence from a gene or an RNA transcript of a gene selected from the group consisting of DEFA4, CD163, PER1, RGS1, HIF1A, SEPP1, C11orf74, CIT, LY86, TST, OR52R1, and KCNJ2. In one embodiment, the panel of biomarkers comprises a DEFA4 polynucleotide, a CD163 polynucleotide, a PER1 polynucleotide, an RGS1 polynucleotide, an HIF1A polynucleotide, a SEPP1 polynucleotide, a C11orf74 polynucleotide, a CIT polynucleotide, LY86 polynucleotide, a TST polynucleotide, an OR52R1 polynucleotide, and a KCNJ2 polynucleotide.

In certain embodiments, a mortality gene score is used for prognosis of mortality risk. The mortality gene score is calculated by subtracting the geometric mean of the expression levels of all measured biomarkers that are underexpressed compared to control reference values for the biomarkers from the geometric mean of the expression levels of all measured biomarkers that are overexpressed compared to control reference values for the biomarkers, and multiplying the difference by the ratio of the number of biomarkers that are overexpressed to the number of biomarkers that are underexpressed compared to control reference values for the biomarkers. A higher mortality gene score for the subject compared to reference value ranges for control subjects indicates that the subject has a high risk of mortality within 30 days (see Example 1).

The methods described herein may be used to identify patients at high risk of mortality who should receive immediate intensive care. For example, patients identified as having a high risk of mortality within 30 days by the methods described herein can be sent immediately to the ICU for treatment, whereas patients identified as having a low risk of mortality within 30 days may be further monitored and/or treated in a regular hospital ward. Both patients and clinicians can benefit from better estimates of mortality risk, which allows timely discussions of patients' preferences and their choices regarding life-saving measures. Better molecular phenotyping of patients also makes possible improvements in clinical trials, both in 1) patient selection for drugs and interventions and 2) assessment of observed-to-expected ratios of subject mortality.

ICU treatment of a patient, identified as having a high risk of mortality within 30 days, may comprise constant monitoring of bodily functions and providing life support equipment and/or medications to restore normal bodily function. ICU treatment may include, for example, using mechanical ventilators to assist breathing, equipment for monitoring bodily functions (e.g., heart and pulse rate, air flow to the lungs, blood pressure and blood flow, central venous pressure, amount of oxygen in the blood, and body temperature), pacemakers, defibrillators, dialysis equipment, intravenous lines, feeding tubes, suction pumps, drains, and/or catheters, and/or administering various drugs for treating the life threatening condition (e.g., sepsis, severe trauma, or burn). ICU treatment may further comprise administration of one or more analgesics to reduce pain, and/or sedatives to induce sleep or relieve anxiety, and/or barbiturates (e.g., pentobarbital or thiopental) to medically induce coma.

In certain embodiments, a critically ill patient diagnosed with a viral infection is further administered a therapeutically effective dose of an antiviral agent, such as a broad-spectrum antiviral agent, an antiviral vaccine, a neuraminidase inhibitor (e.g., zanamivir (Relenza) and oseltamivir (Tamiflu)), a nucleoside analogue (e.g., acyclovir, zidovudine (AZT), and lamivudine), an antisense antiviral agent (e.g., phosphorothioate antisense antiviral agents (e.g., Fomivirsen (Vitravene) for cytomegalovirus retinitis), morpholino antisense antiviral agents), an inhibitor of viral uncoating (e.g., Amantadine and rimantadine for influenza, Pleconaril for rhinoviruses), an inhibitor of viral entry (e.g., Fuzeon for HIV), an inhibitor of viral assembly (e.g., Rifampicin), or an antiviral agent that stimulates the immune system (e.g., interferons). Exemplary antiviral agents include Abacavir, Aciclovir, Acyclovir, Adefovir, Amantadine, Amprenavir, Ampligen, Arbidol, Atazanavir, Atripla (fixed dose drug), Balavir, Cidofovir, Combivir (fixed dose drug), Dolutegravir, Darunavir, Delavirdine, Didanosine, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine.

In certain embodiments, a critically ill patient diagnosed with a bacterial infection is further administered a therapeutically effective dose of an antibiotic. Antibiotics may include broad spectrum, bactericidal, or bacteriostatic antibiotics. Exemplary antibiotics include aminoglycosides such as Amikacin, Amikin, Gentamicin, Garamycin, Kanamycin, Kantrex, Neomycin, Neo-Fradin, Netilmicin, Netromycin, Tobramycin, Nebcin, Paromomycin, Humatin, Streptomycin, Spectinomycin(Bs), and Trobicin; ansamycins such as Geldanamycin, Herbimycin, Rifaximin, and Xifaxan; carbacephems such as Loracarbef and Lorabid; carbapenems such as Ertapenem, Invanz, Doripenem, Doribax, Imipenem/Cilastatin, Primaxin, Meropenem, and Merrem; cephalosporins such as Cefadroxil, Duricef, Cefazolin, Ancef, Cefalotin or Cefalothin, Keflin, Cefalexin, Keflex, Cefaclor, Distaclor, Cefamandole, Mandol, Cefoxitin, Mefoxin, Cefprozil, Cefzil, Cefuroxime, Ceftin, Zinnat, Cefixime, Cefdinir, Cefditoren, Cefoperazone, Cefotaxime, Cefpodoxime, Ceftazidime, Ceftibuten, Ceftizoxime, Ceftriaxone, Cefepime, Maxipime, Ceftaroline fosamil, Teflaro, Ceftobiprole, and Zeftera; glycopeptides such as Teicoplanin, Targocid, Vancomycin, Vancocin, Telavancin, Vibativ, Dalbavancin, Dalvance, Oritavancin, and Orbactiv; lincosamides such as Clindamycin, Cleocin, Lincomycin, and Lincocin; lipopeptides such as Daptomycin and Cubicin; macrolides such as Azithromycin, Zithromax, Surnamed, Xithrone, Clarithromycin, Biaxin, Dirithromycin, Dynabac, Erythromycin, Erythocin, Erythroped, Roxithromycin, Troleandomycin, Tao, Telithromycin, Ketek, Spiramycin, and Rovamycine; monobactams such as Aztreonam and Azactam; nitrofurans such as Furazolidone, Furoxone, Nitrofurantoin, Macrodantin, and Macrobid; oxazolidinones such as Linezolid, Zyvox, VRSA, Posizolid, Radezolid, and Torezolid; penicillins such as Penicillin V, Veetids (Pen-Vee-K), Piperacillin, Pipracil, Penicillin G, Pfizerpen, Temocillin, Negaban, Ticarcillin, and Ticar; penicillin combinations such as Amoxicillin/clavulanate, Augmentin, Ampicillin/sulbactam, Unasyn, Piperacillin/tazobactam, Zosyn, Ticarcillin/clavulanate, and Timentin; polypeptides such as Bacitracin, Colistin, Coly-Mycin-S, and Polymyxin B; quinolones/fluoroquinolones such as Ciprofloxacin, Cipro, Ciproxin, Ciprobay, Enoxacin, Penetrex, Gatifloxacin, Tequin, Gemifloxacin, Factive, Levofloxacin, Levaquin, Lomefloxacin, Maxaquin, Moxifloxacin, Avelox, Nalidixic acid, NegGram, Norfloxacin, Noroxin, Ofloxacin, Floxin, Ocuflox Trovafloxacin, Trovan, Grepafloxacin, Raxar, Sparfloxacin, Zagam, Temafloxacin, and Omniflox; sulfonamides such as Amoxicillin, Novamox, Amoxil, Ampicillin, Principen, Azlocillin, Carbenicillin, Geocillin, Cloxacillin, Tegopen, Dicloxacillin, Dynapen, Flucloxacillin, Floxapen, Mezlocillin, Mezlin, Methicillin, Staphcillin, Nafcillin, Unipen, Oxacillin, Prostaphlin, Penicillin G, Pentids, Mafenide, Sulfamylon, Sulfacetamide, Sulamyd, Bleph-10, Sulfadiazine, Micro-Sulfon, Silver sulfadiazine, Silvadene, Sulfadimethoxine Di-Methox, Albon, Sulfamethizole, Thiosulfil Forte, Sulfamethoxazole, Gantanol, Sulfanilimide, Sulfasalazine, Azulfidine, Sulfisoxazole, Gantrisin, Trimethoprim-Sulfamethoxazole (Co-trimoxazole) (TMP-SMX), Bactrim, Septra, Sulfonamidochrysoidine, and Prontosil; tetracyclines such as Demeclocycline, Declomycin, Doxycycline, Vibramycin, Minocycline, Minocin, Oxytetracycline, Terramycin, Tetracycline and Sumycin, Achromycin V, and Steclin; drugs against mycobacteria such as Clofazimine, Lamprene, Dapsone, Avlosulfon, Capreomycin, Capastat, Cycloserine, Seromycin, Ethambutol, Myambutol, Ethionamide, Trecator, Isoniazid, I.N.H., Pyrazinamide, Aldinamide, Rifampicin, Rifadin, Rimactane, Rifabutin, Mycobutin, Rifapentine, Priftin, and Streptomycin; others antibiotics such as Arsphenamine, Salvarsan, Chloramphenicol, Chloromycetin, Fosfomycin, Monurol, Monuril, Fusidic acid, Fucidin, Metronidazole, Flagyl, Mupirocin, Bactroban, Platensimycin, Quinupristin/Dalfopristin, Synercid, Thiamphenicol, Tigecycline, Tigacyl, Tinidazole, Tindamax Fasigyn, Trimethoprim, Proloprim, and Trimpex.

In another embodiment, the invention includes a method of diagnosing and treating a patient having an infection, the method comprising: a) obtaining a biological sample from the patient; b) measuring levels of expression of DEFA4, CD163, PER1, RGS1, HIF1A, SEPP1, C11orf74, CIT, LY86, TST, OR52R1, and KCNJ2 biomarkers in the biological sample, wherein increased levels of expression of the DEFA4, CD163, PER1, RGS1, HIF1A, SEPP1, C11orf74, and CIT biomarkers and decreased levels of expression of the LY86, TST, OR52R1, and KCNJ2 biomarkers compared to the reference value ranges for the biomarkers for a control subject indicate that the patient has sepsis; and c) administering a sepsis treatment if the patient is diagnosed with sepsis. In some embodiments, the method further comprises calculating a mortality gene score for the patient based on the levels of the biomarkers, wherein a higher mortality gene score for the patient compared to a control subject indicates that the patient is at high risk of mortality within 30 days; and administering intensive care unit treatment to the patient if the patient is at high risk of mortality within 30 days.

Sepsis treatment may comprise, for example, administering antimicrobial therapy, supportive care, or an immune-modulating therapy, or a combination thereof. Antimicrobial therapy may include administration of one or more drugs against all pathogens the patient is likely to be infected with (e.g., bacterial and/or fungal and/or viral) with preferably broad-spectrum coverage using combinations of antimicrobial agents. Combination antimicrobial therapy may include at least two different classes of antibiotics (e.g., a beta-lactam agent with a macrolide, fluoroquinolone, or aminoglycoside). Broad spectrum antibiotics may be administered in combination with antifungal and/or antiviral agents. Supportive therapy for sepsis may include administration of oxygen, blood transfusions, mechanical ventilation, fluid therapy (e.g., fluid administration with crystalloids and/or albumin continued until the patient shows hemodynamic improvement), nutrition (e.g., oral or enteral feedings), blood glucose management, vasopressor therapy (e.g. administration of norepinephrine, epinephrine, and/or vasopressin to maintain adequate blood pressure), inotropic therapy (e.g., dobutamine), renal replacement therapy (e.g., dialysis), bicarbonate therapy, pharmacoprophylaxis against venous thromboembolism (e.g., treatment with heparin or intermittent pneumatic compression device), stress ulcer prophylaxis, sedation, analgesia, neuromuscular blockade, insulin (e.g., to maintain stable blood sugar levels), or corticosteroids (e.g., hydrocortisone), or any combination thereof. Immune-modulating therapy may include administration of activated protein C, immunoglobulin therapy, anti-platelet therapy, cytokine-blocking therapy, dialysis for pathogenic proteins or with antibiotic cartridges, or any combination thereof.

B. Detecting and Measuring Biomarkers

It is understood that the biomarkers in a sample can be measured by any suitable method known in the art. Measurement of the expression level of a biomarker can be direct or indirect. For example, the abundance levels of RNAs or proteins can be directly quantitated. Alternatively, the amount of a biomarker can be determined indirectly by measuring abundance levels of cDNAs, amplified RNAs or DNAs, or by measuring quantities or activities of RNAs, proteins, or other molecules (e.g., metabolites) that are indicative of the expression level of the biomarker. The methods for measuring biomarkers in a sample have many applications. For example, one or more biomarkers can be measured to aid in the prognosis of mortality risk, to determine the appropriate treatment for a subject, to monitor responses in a subject to treatment, or to identify therapeutic compounds that modulate expression of the biomarkers in vivo or in vitro.

Detecting Biomarker Polynucleotides

In one embodiment, the expression levels of the biomarkers are determined by measuring polynucleotide levels of the biomarkers. The levels of transcripts of specific biomarker genes can be determined from the amount of mRNA, or polynucleotides derived therefrom, present in a biological sample. Polynucleotides can be detected and quantitated by a variety of methods including, but not limited to, microarray analysis, polymerase chain reaction (PCR), reverse transcriptase polymerase chain reaction (RT-PCR), Northern blot, and serial analysis of gene expression (SAGE). See, e.g., Draghici *Data Analysis Tools for DNA Microarrays*, Chapman and Hall/CRC, 2003; Simon et al. *Design and Analysis of DNA Microarray Investigations*, Springer, 2004; *Real-Time PCR: Current Technology and Applications*, Logan, Edwards, and Saunders eds., Caister Academic Press, 2009; Bustin *A-Z of Quantitative PCR* (IUL Biotechnology, No. 5), International University Line, 2004; Velculescu et al. (1995) Science 270: 484-487; Matsumura et al. (2005) Cell. Microbiol. 7: 11-18; *Serial Analysis of Gene Expression (SAGE): Methods and Protocols (Methods in Molecular Biology)*, Humana Press, 2008; herein incorporated by reference in their entireties.

In one embodiment, microarrays are used to measure the levels of biomarkers. An advantage of microarray analysis is that the expression of each of the biomarkers can be measured simultaneously, and microarrays can be specifically designed to provide a diagnostic expression profile for a particular disease or condition (e.g., sepsis).

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well known in the art (see, e.g., Sambrook, et al., *Molecular Cloning: A Laboratory Manual* (3rd Edition, 2001). Alternatively, the solid support or surface may be a glass or plastic surface. In one embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In one embodiment, the microarray comprises a support or surface with an ordered array of binding (e.g., hybridization) sites or "probes" each representing one of the biomarkers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Microarrays can be made in a number of ways, of which several are described below. However they are produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 1 $cm^2$ and 25 $cm^2$; however, larger arrays may also be used, e.g., in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., *PCR Protocols: A Guide To Methods And Applications*, Academic Press Inc., San Diego, Calif. (1990); herein incorporated by reference in its entirety. It will be apparent to one skilled in the art that controlled robotic systems are useful for isolating and amplifying nucleic acids.

An alternative, preferred means for generating polynucleotide probes is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., Nature 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., Nat. Biotech. 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. One method for attaching nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995); herein incorporated by reference in their entireties).

A second method for making microarrays produces high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270; herein incorporated by reference in their entireties) or other methods for rapid synthesis and deposition of defined oligonucleotides (Blanchard et al., Biosensors & Bioelectronics 11:687-690; herein incorporated by reference in its entirety). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids. Res. 20:1679-1684; herein incorporated by reference in its entirety), may also be used. In principle, any type of array, for example, dot blots on a nylon hybridization membrane (see Sambrook, et al., *Molecular Cloning: A Laboratory Manual*, 3rd Edition, 2001) could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123; herein incorporated by reference in their entireties. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 $cm^2$. The polynucleotide probes are attached to the support covalently at either the 3' or the 5' end of the polynucleotide.

Biomarker polynucleotides which may be measured by microarray analysis can be expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly(A)$^+$ messenger RNA (mRNA) or a fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly(A)$^+$ RNA are well known in the art, and are described generally, e.g., in Sambrook, et al., *Molecular Cloning: A Laboratory Manual* (3rd Edition, 2001). RNA can be extracted from a cell of interest using guanidinium thiocyanate lysis followed by CsCl centrifugation (Chirgwin et al., 1979, Biochemistry 18:5294-5299), a silica gel-based column (e.g., RNeasy (Qiagen, Valencia, Calif.) or StrataPrep (Stratagene, La Jolla, Calif.)), or using phenol and chloroform, as described in Ausubel et al., eds., 1989, *Current Protocols In Molecular Biology*, Vol. III, Green Publishing Associates, Inc., John Wiley & Sons, Inc., New York, at pp. 13.12.1-13.12.5). Poly(A)$^+$ RNA can be selected, e.g., by selection with oligo-dT cellulose or, alternatively, by oligo-dT primed reverse transcription of total cellular RNA. RNA can be fragmented by methods known in the art, e.g., by incubation with $ZnCl_2$, to generate fragments of RNA.

In one embodiment, total RNA, mRNA, or nucleic acids derived therefrom, are isolated from a sample taken from a patient suspected of having a life-threatening condition (e.g., sepsis, severe trauma, or burn). Biomarker polynucleotides that are poorly expressed in particular cells may be enriched using normalization techniques (Bonaldo et al., 1996, Genome Res. 6:791-806).

As described above, the biomarker polynucleotides can be detectably labeled at one or more nucleotides. Any method known in the art may be used to label the target polynucleotides. Preferably, this labeling incorporates the label uniformly along the length of the RNA, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Additionally, commercially available fluorescent labels including, but not limited to, fluorescent phosphoramidites such as FluorePrime (Amersham Pharmacia, Piscataway, N.J.), Fluoredite (Miilipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

In one embodiment, biomarker polynucleotide molecules from a patient sample are labeled differentially from the corresponding polynucleotide molecules of a reference sample. The reference can comprise polynucleotide molecules from a normal biological sample (i.e., control sample, e.g., blood from a survivor or a subject not having sepsis/infection, burn, or trauma) or from a reference biological sample, (e.g., blood from a non-survivor or a subject having sepsis/infection, burn, or trauma).

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., *Molecular Cloning: A Laboratory Manual* (3rd Edition, 2001), and in Ausubel et al., *Current Protocols In Molecular Biology*, vol. 2, Current Protocols Publishing, New York (1994). Typical hybridization conditions for the cDNA microarrays of Schena et al. are hybridization in 5.times.SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, *Hybridization With Nucleic Acid Probes*, Elsevier Science Publishers B.V.; and Kricka, 1992, *Nonisotopic Dna Probe Techniques*, Academic Press, San Diego, Calif. Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," Genome Research 6:639-645, which is incorporated by reference in its entirety for all purposes). Arrays can be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously.

In one embodiment, the invention includes a microarray comprising an oligonucleotide that hybridizes to an oligonucleotide that hybridizes to a DEFA4 polynucleotide, an oligonucleotide that hybridizes to a CD163 polynucleotide, an oligonucleotide that hybridizes to a PER1 polynucleotide, an oligonucleotide that hybridizes to a RGS1 polynucleotide, an oligonucleotide that hybridizes to an HIF1A polynucleotide, an oligonucleotide that hybridizes to a SEPP1 polynucleotide, an oligonucleotide that hybridizes to a C11orf74 polynucleotide, an oligonucleotide that hybridizes to a CIT polynucleotide, an oligonucleotide that hybridizes to a LY86 polynucleotide, an oligonucleotide that hybridizes to a TST polynucleotide, an oligonucleotide that hybridizes to an OR52R1 polynucleotide, and an oligonucleotide that hybridizes to a KCNJ2 polynucleotide.

Polynucleotides can also be analyzed by other methods including, but not limited to, northern blotting, nuclease protection assays, RNA fingerprinting, polymerase chain reaction, ligase chain reaction, Qbeta replicase, isothermal amplification method, strand displacement amplification, transcription based amplification systems, nuclease protection (Si nuclease or RNAse protection assays), SAGE as well as methods disclosed in International Publication Nos. WO 88/10315 and WO 89/06700, and International Applications Nos. PCT/US87/00880 and PCT/US89/01025; herein incorporated by reference in their entireties.

A standard Northern blot assay can be used to ascertain an RNA transcript size, identify alternatively spliced RNA transcripts, and the relative amounts of mRNA in a sample, in accordance with conventional Northern hybridization techniques known to those persons of ordinary skill in the art. In Northern blots, RNA samples are first separated by size by electrophoresis in an agarose gel under denaturing conditions. The RNA is then transferred to a membrane, cross-linked, and hybridized with a labeled probe. Nonisotopic or high specific activity radiolabeled probes can be used, including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Isotopes that can be used include, but are not limited to, $^{3}H$, $^{14}C$, $^{32}P$, $^{35}S$, $^{36}Cl$, $^{35}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays (including both ribonuclease protection assays and Si nuclease assays) can be used to detect and quantitate specific mRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

The ribonuclease protection assay, which is the most common type of nuclease protection assay, requires the use of RNA probes. Oligonucleotides and other single-stranded DNA probes can only be used in assays containing 51 nuclease. The single-stranded, antisense probe must typically be completely homologous to target RNA to prevent cleavage of the probe:target hybrid by nuclease.

Serial Analysis Gene Expression (SAGE) can also be used to determine RNA abundances in a cell sample. See, e.g., Velculescu et al., 1995, Science 270:484-7; Carulli, et al., 1998, Journal of Cellular Biochemistry Supplements 30/31: 286-96; herein incorporated by reference in their entireties.

SAGE analysis does not require a special device for detection, and is one of the preferable analytical methods for simultaneously detecting the expression of a large number of transcription products. First, poly A+ RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the ITS-type restriction enzyme (cleaves at a predetermined location no more than 20 bp away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified from the nucleotide sequence of the clone and information on the sequence tags.

Quantitative reverse transcriptase PCR (qRT-PCR) can also be used to determine the expression profiles of biomarkers (see, e.g., U.S. Patent Application Publication No. 2005/0048542A1; herein incorporated by reference in its entirety). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 sequence detection system. (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 sequence detection system. The system consists of a thermocycler, laser, charge-coupled device (CCD), camera and computer. The system includes software for running the instrument and for analyzing the data. 5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

A more recent variation of the RT-PCR technique is the real time quantitative PCR, which measures PCR product accumulation through a dual-labeled fluorogenic probe (i.e., TAQMAN probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

Analysis of Biomarker Data

Biomarker data may be analyzed by a variety of methods to identify biomarkers and determine the statistical significance of differences in observed levels of biomarkers between test and reference expression profiles in order to evaluate whether a patient is at risk of mortality within 30 days. In certain embodiments, patient data is analyzed by one or more methods including, but not limited to, multivariate linear discriminant analysis (LDA), receiver operating characteristic (ROC) analysis, principal component analysis (PCA), ensemble data mining methods, significance analysis of microarrays (SAM), cell specific significance analysis of microarrays (csSAM), spanning-tree progression analysis of density-normalized events (SPADE), and multidimensional protein identification technology (MUDPIT) analysis. (See, e.g., Hilbe (2009) Logistic Regression Models, Chapman & Hall/CRC Press; McLachlan (2004) Discriminant Analysis and Statistical Pattern Recognition. Wiley Interscience; Zweig et al. (1993) Clin. Chem. 39:561-

577; Pepe (2003) The statistical evaluation of medical tests for classification and prediction, New York, N.Y.: Oxford; Sing et al. (2005) Bioinformatics 21:3940-3941; Tusher et al. (2001) Proc. Natl. Acad. Sci. U.S.A. 98:5116-5121; Oza (2006) Ensemble data mining, NASA Ames Research Center, Moffett Field, Calif., USA; English et al. (2009) J. Biomed. Inform. 42(2):287-295; Zhang (2007) Bioinformatics 8: 230; Shen-Orr et al. (2010) Journal of Immunology 184:144-130; Qiu et al. (2011) Nat. Biotechnol. 29(10):886-891; Ru et al. (2006) J. Chromatogr. A. 1111(2):166-174, Jolliffe Principal Component Analysis (Springer Series in Statistics, $2^{nd}$ edition, Springer, N.Y., 2002), Koren et al. (2004) IEEE Trans Vis Comput Graph 10:459-470; herein incorporated by reference in their entireties.)

C. Kits

In yet another aspect, the invention provides kits for prognosis of mortality in a subject, wherein the kits can be used to detect the biomarkers of the present invention. For example, the kits can be used to detect any one or more of the biomarkers described herein, which are differentially expressed in samples from survivors and non-survivors in critically ill patients. The kit may include one or more agents for detection of biomarkers, a container for holding a biological sample isolated from a human subject suspected of having a life-threatening condition; and printed instructions for reacting agents with the biological sample or a portion of the biological sample to detect the presence or amount of at least one biomarker in the biological sample. The agents may be packaged in separate containers. The kit may further comprise one or more control reference samples and reagents for performing an immunoassay or microarray analysis.

In certain embodiments, the kit comprises agents for measuring the levels of at least twelve biomarkers of interest. For example, the kit may include agents for detecting biomarkers of a panel comprising a DEFA4 polynucleotide, a CD163 polynucleotide, a PER1 polynucleotide, a RGS1 polynucleotide, an HIF1A polynucleotide, a SEPP1 polynucleotide, a C11orf74 polynucleotide, a CIT polynucleotide, LY86 polynucleotide, a TST polynucleotide, an OR52R1 polynucleotide, and a KCNJ2 polynucleotide.

In certain embodiments, the kit comprises a microarray for analysis of a plurality of biomarker polynucleotides. An exemplary microarray included in the kit comprises an oligonucleotide that hybridizes to a DEFA4 polynucleotide, an oligonucleotide that hybridizes to a CD163 polynucleotide, an oligonucleotide that hybridizes to a PER1 polynucleotide, an oligonucleotide that hybridizes to a RGS1 polynucleotide, an oligonucleotide that hybridizes to an HIF1A polynucleotide, an oligonucleotide that hybridizes to a SEPP1 polynucleotide, an oligonucleotide that hybridizes to a C11orf74 polynucleotide, an oligonucleotide that hybridizes to a CIT polynucleotide, an oligonucleotide that hybridizes to a LY86 polynucleotide, an oligonucleotide that hybridizes to a TST polynucleotide, an oligonucleotide that hybridizes to an OR52R1 polynucleotide, and an oligonucleotide that hybridizes to a KCNJ2 polynucleotide.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of diagnosing sepsis.

The kits of the invention have a number of applications. For example, the kits can be used to determine the mortality risk of a subject suspected of having a life-threatening condition. Subjects identified as having a high risk of mortality within 30 days by the methods described herein can be sent to the ICU for treatment, whereas patients identified as having a low risk of mortality within 30 days may be further monitored and/or treated in a regular hospital ward. Both patients and clinicians can benefit from better estimates of mortality risk, which allows timely discussions of patient preferences and their choices regarding life-saving measures. Better molecular phenotyping of patients also makes possible improvements in clinical trials, both in 1) patient selection for drugs and interventions and 2) assessment of observed-to-expected ratios of subject mortality.

D. Diagnostic System and Computerized Methods for Determining Mortality Risk

In a further aspect, the invention includes a computer implemented method for determining mortality risk of a patient suspected of having a life-threatening condition. The computer performs steps comprising: receiving inputted patient data comprising values for the levels of one or more biomarkers in a biological sample from the patient; analyzing the levels of one or more biomarkers and comparing with respective reference value ranges for the biomarkers; calculating a mortality gene score for the patient based on the levels of the biomarkers, wherein a higher mortality gene score for the patient compared to a control subject indicates that the patient is at high risk of mortality within 30 days; and displaying information regarding the mortality risk of the patient. In certain embodiments, the inputted patient data comprises values for the levels of a plurality of biomarkers in a biological sample from the patient. In one embodiment, the inputted patient data comprises values for the levels of DEFA4, CD163, PER1, RGS1, HIF1A, SEPP1, C11orf74, CIT, LY86, TST, OR52R1, and KCNJ2 polynucleotides.

In a further aspect, the invention includes a diagnostic system for performing the computer implemented method, as described. A diagnostic system may include a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for determining the mortality risk of the subject. For example, the storage component includes instructions for calculating the mortality gene score for the subject based on biomarker expression levels, as described herein (e.g., see Example 1). In addition, the storage component may further comprise instructions for performing multivariate linear discriminant analysis (LDA), receiver operating characteristic (ROC) analysis, principal component analysis (PCA), ensemble data mining methods, cell specific significance analysis of microarrays (csSAM), or multi-dimensional protein identification technology (MUDPIT) analysis. The computer processor is coupled to the storage component and configured to execute the instructions stored in the storage component in order to receive patient data and analyze patient data according to one or more algorithms. The display component displays information regarding the diagnosis and/or prognosis (e.g., mortality risk) of the patient.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

In one aspect, computer is a server communicating with one or more client computers. Each client computer may be configured similarly to the server, with a processor, storage component and instructions. Each client computer may be a personal computer, intended for use by a person, having all the internal components normally found in a personal computer such as a central processing unit (CPU), display (for example, a monitor displaying information processed by the processor), CD-ROM, hard-drive, user input device (for example, a mouse, keyboard, touch-screen or microphone), speakers, modem and/or network interface device (telephone, cable or otherwise) and all of the components used for connecting these elements to one another and permitting them to communicate (directly or indirectly) with one another. Moreover, computers in accordance with the systems and methods described herein may comprise any device capable of processing instructions and transmitting data to and from humans and other computers including network computers lacking local storage capability.

Although the client computers and may comprise a full-sized personal computer, many aspects of the system and method are particularly advantageous when used in connection with mobile devices capable of wirelessly exchanging data with a server over a network such as the Internet. For example, client computer may be a wireless-enabled PDA such as a Blackberry phone, Apple iPhone, Android phone, or other Internet-capable cellular phone. In such regard, the user may input information using a small keyboard, a keypad, a touch screen, or any other means of user input. The computer may have an antenna for receiving a wireless signal.

The server and client computers are capable of direct and indirect communication, such as over a network. Although only a few computers may be used, it should be appreciated that a typical system can include a large number of connected computers, with each different computer being at a different node of the network. The network, and intervening nodes, may comprise various combinations of devices and communication protocols including the Internet, World Wide Web, intranets, virtual private networks, wide area networks, local networks, cell phone networks, private networks using communication protocols proprietary to one or more companies, Ethernet, WiFi and HTTP. Such communication may be facilitated by any device capable of transmitting data to and from other computers, such as modems (e.g., dial-up or cable), networks and wireless interfaces. The server may be a web server.

Although certain advantages are obtained when information is transmitted or received as noted above, other aspects of the system and method are not limited to any particular manner of transmission of information. For example, in some aspects, information may be sent via a medium such as a disk, tape, flash drive, DVD, or CD-ROM. In other aspects, the information may be transmitted in a non-electronic format and manually entered into the system. Yet further, although some functions are indicated as taking place on a server and others on a client, various aspects of the system and method may be implemented by a single computer having a single processor.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Methods for Prognosis of Mortality in Critically Ill Patients

Introduction

We have previously shown that multi-cohort analysis is an effective way to find conserved gene expression signals in sepsis[15] and other diseases including organ transplant rejection, viral infections, and pulmonary tuberculosis[16-18]. We thus hypothesized that a multi-cohort analysis examining outcomes in patients with sepsis would yield a conserved gene set that could robustly predict sepsis outcomes, and potentially be used as a clinical tool for disease prognosis.

Materials and Methods

Study Design

The purpose of this study was to use an integrated multi-cohort meta-analysis framework to analyze multiple gene expression datasets to identify a set of genes that can predict mortality in patients with sepsis, at the time of admission. This framework has been described previously[15, 16, 18].

Search

Two public gene expression microarray repositories (NIH GEO, ArrayExpress) were searched for all human datasets that matched any of the following search terms: sepsis, SIRS, trauma, shock, surgery, infection, pneumonia, critical, ICU, inflammatory, nosocomial. Datasets that compared either healthy controls or patients with non-infectious inflammation (SIRS, trauma, surgery, autoimmunity) to patients with acute infections and/or sepsis were kept for further study. Datasets that utilized endotoxin injection as a model for SIRS or sepsis were not included. Datasets done in sorted cells (PBMCs, neutrophils, etc.), were excluded.

In many cases, mortality and severity phenotypes were not available in the public data; these authors were contacted for further data. This included datasets E-MTAB-1548[12], GSE10474[19], G5E21802[20], GSE32707[21], GSE33341[22], GSE63042[11], GSE63990[23], GSE66099[10,15,24,25], and GSE66890[26]. In all cases, gene expression data are publicly available. The investigators who contributed these data did not participate in the data analysis described below.

The two cohorts E-MTAB-4421 and E-MTAB-4451 came from the same study (GaINs)[14], with the same inclusion/exclusion criteria, and were processed on the same microarrays. Thus, after re-normalizing from raw data, we used ComBat normalization to co-normalize these two cohorts into a single cohort, which we refer to as E-MTAB-4421.51.

Glue Grant Data

In addition to the publicly-available datasets, we used the Inflammation and Host Response to Injury Program (Glue Grant) trauma datasets[27-29]. The Glue Grant datasets contain two cohorts: patients admitted with severe trauma, and patients admitted with severe burns. The trauma cohorts further include two sub-cohorts, one which sampled buffy coat, and the other which sampled sorted cells; the sorted-cells cohort were excluded from further study. Inclusion criteria are described elsewhere[30]. Trauma patients were sampled at the following days after admission: 0.5, 1, 4, 7, 14, 21, 28 days; Burn patients were sampled at admission, and then at the time of their burn operations. The Glue Grant patients were classified as 'infected' if they had a nosocomial infection (pneumonia, urinary tract infection, catheter-related bloodstream infection, etc.), a surgical infection (excluding superficial wound infections), or underwent surgery for perforated viscus; infection definitions can be found at gluegrant.org/commonlyreferencedpubs.htm. Samples drawn within +/−24 hours of the day of diagnosis of infection were considered to be time of infection. Use of the Glue Grant was approved by both the Glue Grant Consortium and the Stanford University IRB (protocol 29798).

Gene Expression Normalization

All Affymetrix datasets were downloaded as CEL files and re-normalized using gcRMA (R package affy). Output from other arrays were normal-exponential background corrected and then between-arrays quantile normalized (R package limma). For all gene analyses, the mean of probes for common genes was set as the gene expression level. All probe-to-gene mappings were downloaded from GEO from the most current SOFT files.

Multi-Cohort Analysis

We performed a multi-cohort analysis[15,16,18] of gene expression in sepsis patients within 48 hours of admission comparing patients who died within 30 days to patients who did not. In the rare case where we had information on which patients died after 30 days, these patients were excluded. After selecting the input datasets, we combined effect sizes within cohorts using Hedges' g, and then evaluated summary effects with a DerSimonian-Laird meta-analysis. Significance thresholds were set at a false discovery rate (FDR) of 0.05, with a summary effect size greater than 1.3 fold (in non-log space).

We next performed a meta-regression analysis in the cohorts which supplied phenotype data of clinical severity and age. For each cohort, for each gene, the model was a regression on mortality (dependent) as a function of clinical severity plus age plus gene expression level. To keep the scales between datasets similar, (1) all clinical severity scores were converted to log-odds mortality, based on models in their describing papers, and (2) all datasets were ComBat-normalized together prior to meta-analysis (this method resets the location and scale of each gene, but within-cohort differences are preserved). The meta-regression was carried out using the closed-form method-of-moments random-effects model variation[31] of the synthesis-of-slopes regression method described by Becker and Wu (2007)[32]. Thus, in this case, a gene was considered to be significant if it had statistically conserved regression coefficients (betas) across all cohorts for the prediction of mortality independent of clinical severity and age. An uncorrected p value <0.01 was deemed significant.

In the final step of the analysis, we took as significant the union of the gene sets deemed to be significant both by standard multi-cohort analysis and by meta-regression. These genes were then used in a greedy iterated search model, where a greedy forward search was allowed to run to completion, followed by a greedy backward search, and then another greedy forward search. This method iterated until it reached a stable gene set. Only the discovery datasets were used in the search, and the functions maximized the weighted AUC, which is the sum of the AUC of each discovery dataset multiplied by its sample size.

Gene Score

In the greedy search, and with the final gene set, the gene score is defined as the geometric mean of the gene expression level for all positive genes minus the geometric mean of the gene expression level of all negative genes multiplied by the ratio of counts of positive to negative genes. This was calculated for each sample in a dataset separately. Genes not present in an entire dataset were excluded; genes missing for individual samples were set to one.

ROC Curves

Class discriminatory power was examined comparing the gene scores for classes of interest in each examined dataset. ROC curves of the gene score were constructed within datasets, and the area under the curve (AUC) was calculated using the trapezoidal method. Summary ROC curves were calculated via the method of Kester and Buntinx, as previously described[18,33]. Summary curves were only used to summarize data from similar comparisons (i.e., sepsis patients at admission).

Comparison with Severity Scores

We compared the prognostic power of the gene score with the prognostic power of the clinical severity scores in all cohorts which contained this information. To do these calculations, we first performed logistic regression on either the clinical severity score or the gene score to predict mortality. We then tested a combined model (mortality as a function of clinical severity and gene score, without interaction term) and measured the AUC of the combined model.

Validation

The main validation examined patients admitted to the hospital with sepsis, comparing survivors with eventual non-survivors, as determined by each study's original investigators. In the case of datasets with longitudinal data, only the patients within the first 24-48 hours since admission were used in the summary ROC analysis. ROC plots were constructed separately for patients at later time points, broken into bins by day since admission, depending on each study's sampling schema.

Custom analyses were used to study the performance of the gene set in the Glue Grant datasets. First, all patients in each dataset (trauma and burns) were plotted by day since injury for both gene score and daily severity score (for the trauma patients, this was the MODS score; for the burn patients, this was the Denver score). Death type was enumerated as per the original definitions by the Glue Grant authors: either (1) sepsis death, (2) traumatic brain injury (TBI)/brain death, or (3) other death. We split out TBI/brain death as these deaths are often primarily direct sequalae of the initial injury, rather than being caused by host response. In the burns cohort, several patients were noted to die during the study period but after 30 days; these patients were excluded. We then performed two types of ROC analysis. In the first, we examined patients who contracted sepsis who eventually died, and compared them with patients who contracted sepsis but did not die, but only those patients who contracted sepsis within the same time window were included. This is analogous to examining only the day of admission in the community-acquired sepsis cohorts. In the second ROC analysis, we examined all patients, comparing patients who died of any cause to those who did not. Here we split the groups into bins by time since admission; however, some patients were thus repeated between these groups, and so for the all-cause mortality analysis, the different time-bins are not independent.

Cell-Type Enrichment Tests

Gene sets were evaluated for enrichment in previously examined in vitro immune cell profiles as previously described[15]. Briefly, GEO was searched for gene expression profiles of clinical samples of relevant immune cell types. For multiple samples all corresponding to the same cell type, the mean of the samples was taken as the final value, thus creating a single vector for each cell type. Gene scores for each gene set were calculated in the resulting cell-type vectors as described above. These scores are then standardized across all cell types, such that the score represents the number of standard deviations away from the group mean. This thus represents how enriched a given gene set is in a given cell type, relative to other tested cell types.

Two gene sets were tested in this manner: both the entire set of genes found to be significant after the multi-cohort/meta-regress analysis, and the subset of genes found to be most diagnostic after the iterated greedy search. Resulting plots show the Z-score (enrichment for the given gene set) in each cell subtype (black dots), as well as a box plot for the overall distribution of Z-scores (shown in red).

Statistics and R

All computation and calculations were carried out in the R language for statistical computing (version 3.2.0). Significance levels for p-values were set at 0.05, and analyses were two-tailed, unless specified otherwise.

Results

Analysis Overview

Our systematic search revealed 19 cohorts that matched inclusion/exclusion criteria[9,11,12,14,15,19-23,26,34-38]. Of these, we prospectively identified two datasets as validation cohorts: GSE54514 and E-MTAB-4421.51. The other validation datasets (GSE21802, GSE33341, GSE63990) only had the phenotype data become available after analysis was completed. Thus, in the remaining datasets, we took all those which specifically examined sepsis patients at admission to the hospital or to the ICU, which yielded 12 cohorts, with a total of 490 survivors and 160 non-survivors (Table 1). We applied two analytic methods to discover genes significantly associated with mortality (FIG. 1). In the first, we performed multi-cohort meta-analysis for differential gene expression between survivors and non-survivors at admission, yielding 96 genes significant at FDR<0.05 and effect size >1.3-fold. In the second analysis, we performed synthesis-of-slopes random-effects meta-regression for mortality as a logistic function of clinical severity, age, and gene expression. This yielded 35 genes significant at p<0.01. Notably, the top three most-significant genes in the meta-regression were all from the same pathway, namely, neutrophil azurophilic granules: DEFA4, CTSG, and MPO. The union of the meta-analysis and meta-regression gene sets was 122 genes, which we took as our 'significant' gene list.

Discovery of the 12-Gene Set

We next used the 122-gene list to perform an iterated greedy search on the 12 discovery datasets, trying to find a gene list which maximized diagnostic performance, as measured by weighted AUC. Briefly, the algorithm iterates between a forward and backward greedy search, until it converges on a gene list. This algorithm is designed to find maxima closer to the global maximum than a simple forward search. The algorithm ran to completion, producing a 12-gene set. The genes upregulated in patients with mortality were: DEFA4, CD163, PER1, RGS1, HIF1A, SEPP1, C11orf74, and CIT, and the downregulated genes were: LY86, TST, OR52R1, and KCNJ2. This 12-gene set had a mean discovery AUC of 0.847+/−0.081, with a summary AUC of 0.85 (FIGS. 2-6). In addition, in comparing the mortality gene score with the clinical severity score in the discovery cohorts, we showed that in all cases, the gene score improved upon the prediction of mortality using clinical severity alone (except in two cases where clinical severity perfectly separated mortality; Table 2). Finally, only one cohort (GSE63042) contained blood lactate levels; in this group, the blood lactate AUC was 0.72, while the 12-gene score AUC was 0.78.

Direct Validation in Sepsis Patients at Admission

Figure 7:
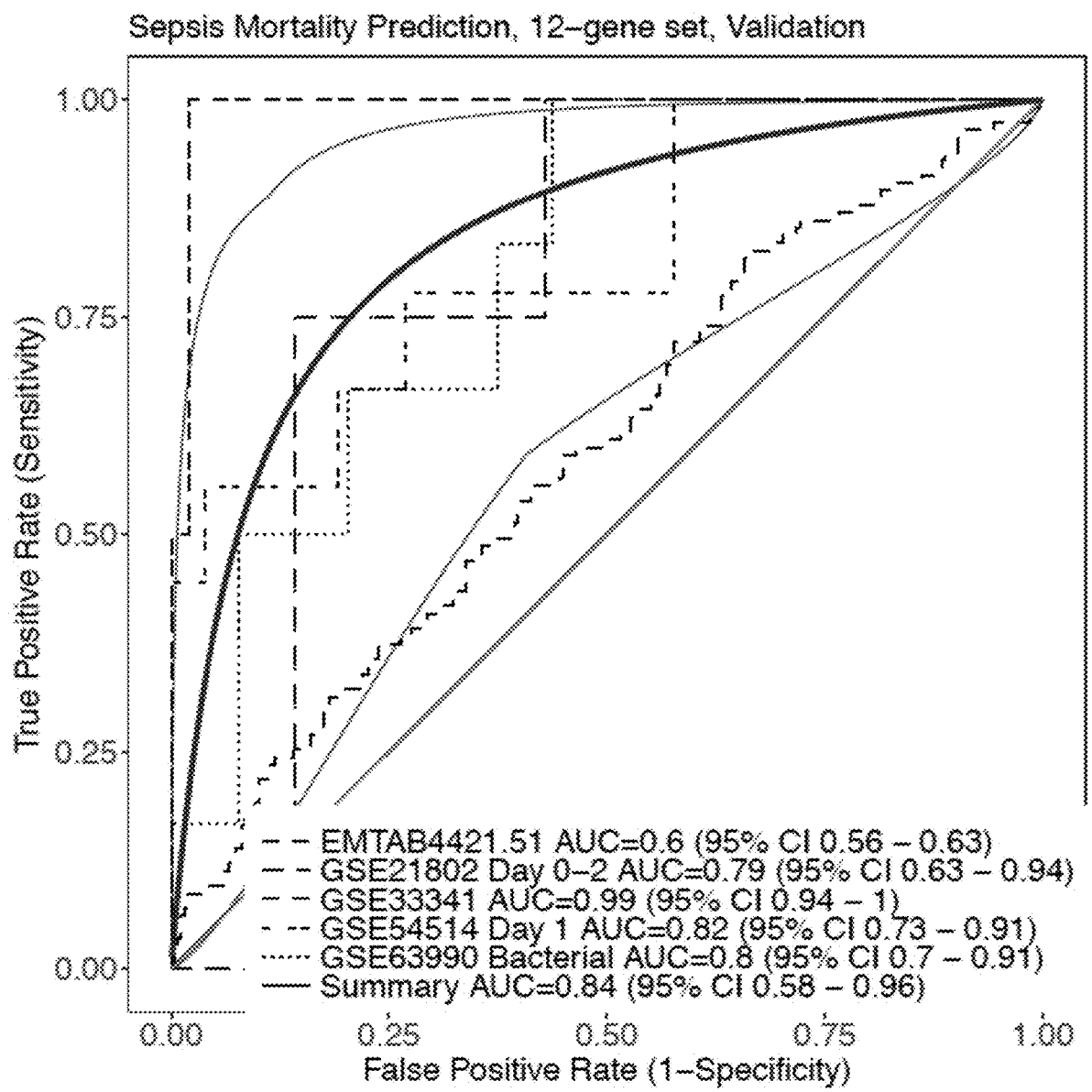
FIG. 7 shows summary ROC curves from validation datasets. Shown is the prognostic power of the 12-gene set for prediction of mortality in septic patients at admission.
Figure 8:
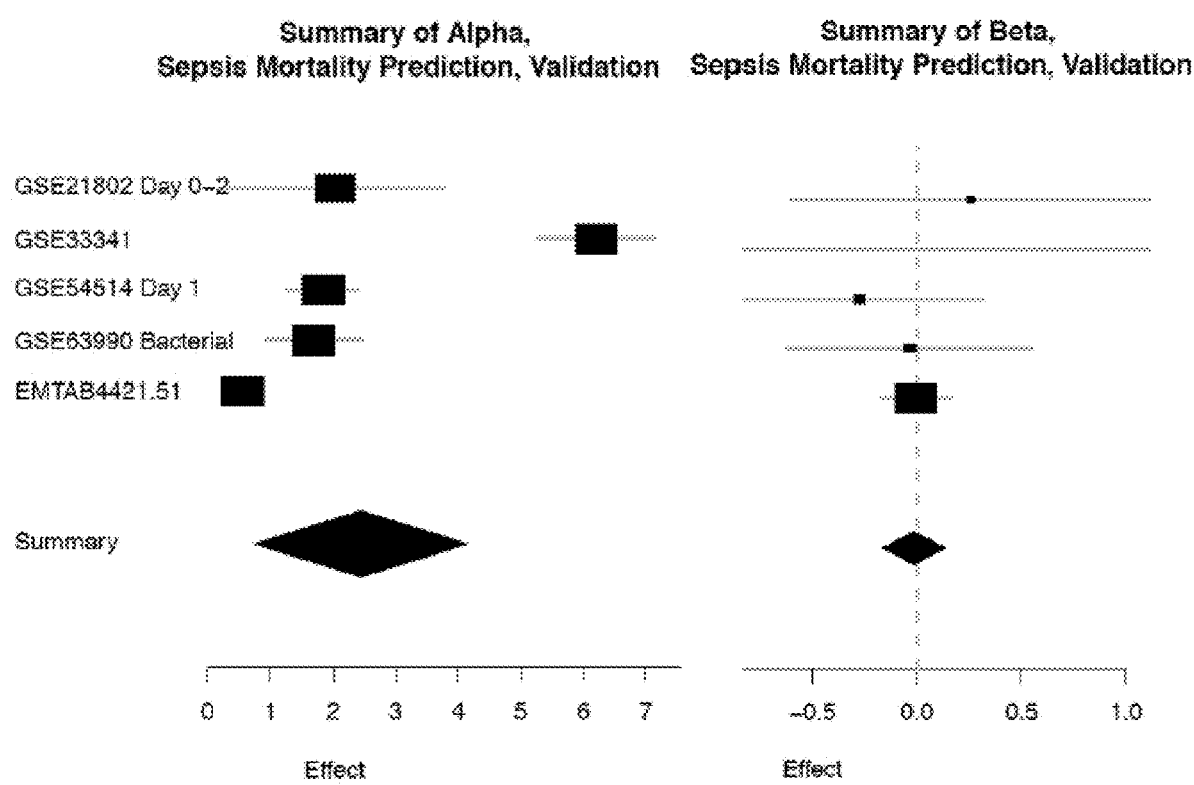
FIG. 8 shows Forest plots of the alpha and beta parameters for the summary ROC curve in the validation datasets from FIG. 7.
Figure 9:
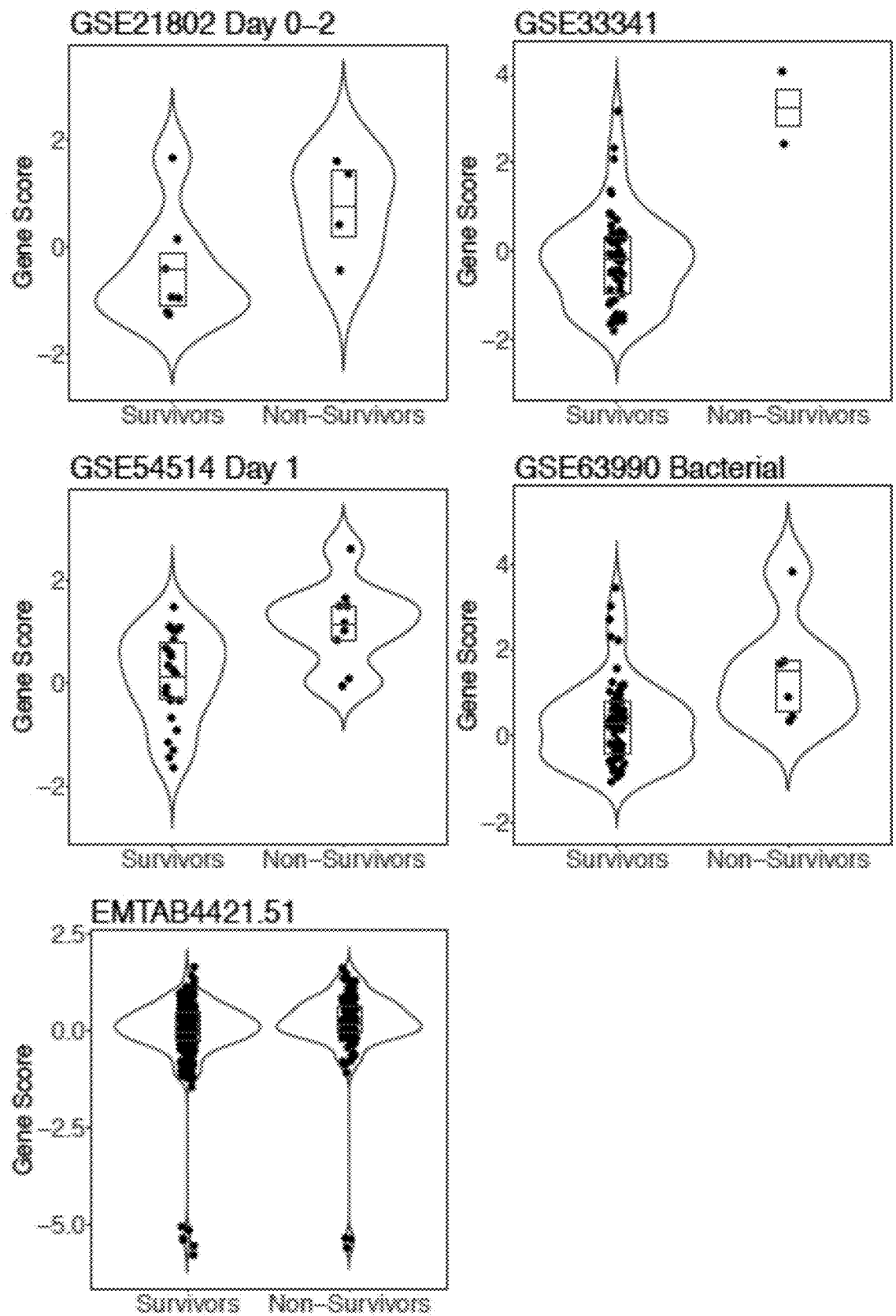
FIG. 9 shows violin plots of the 12-gene scores for individual patients in the validation cohorts, separate by survivor status. Inner bars show mean and inter-quartile range.
Figure 10A:
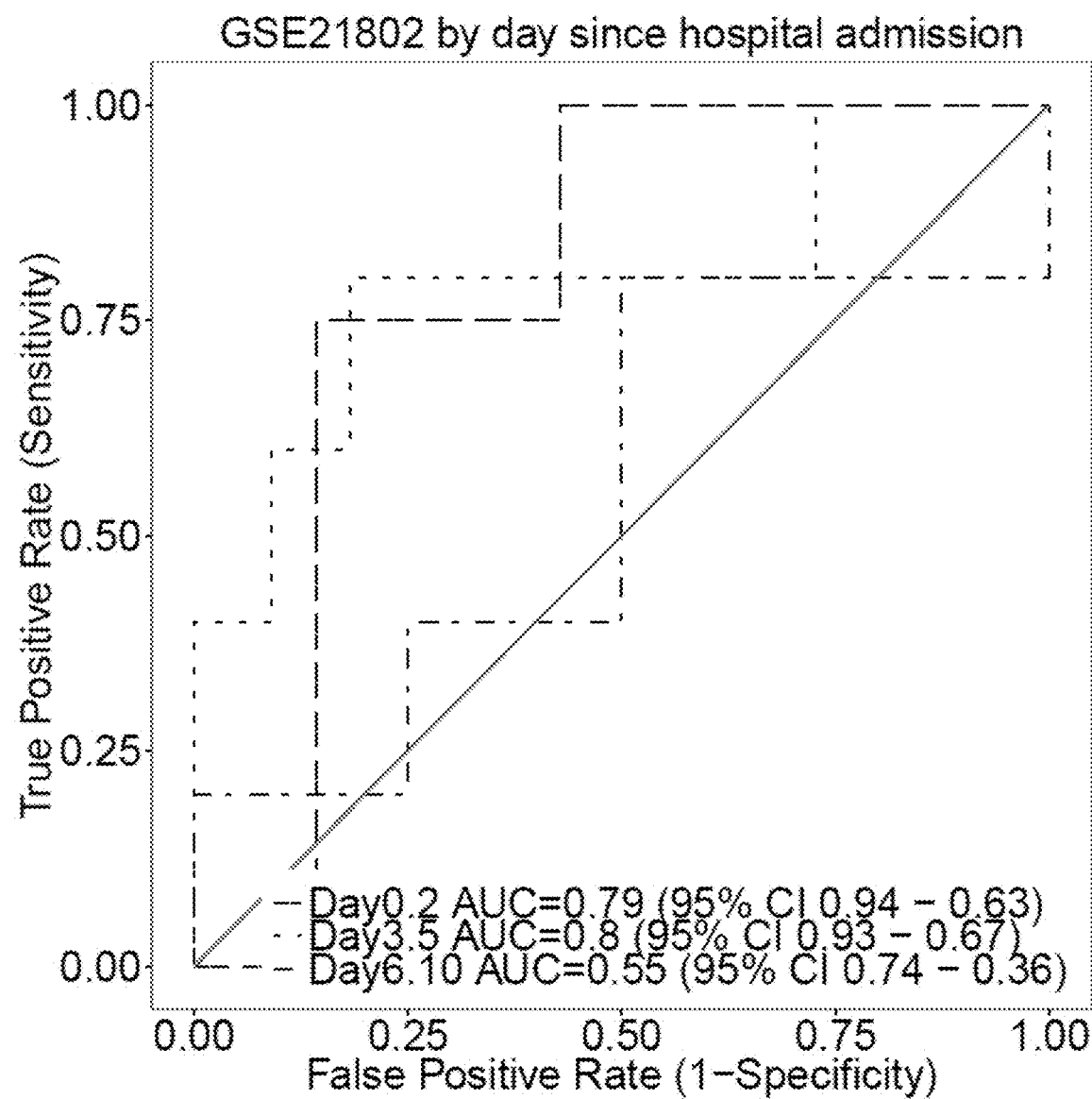
FIGS. 10A and 10B show longitudinal data from validation dataset GSE21802.
Figure 10B:
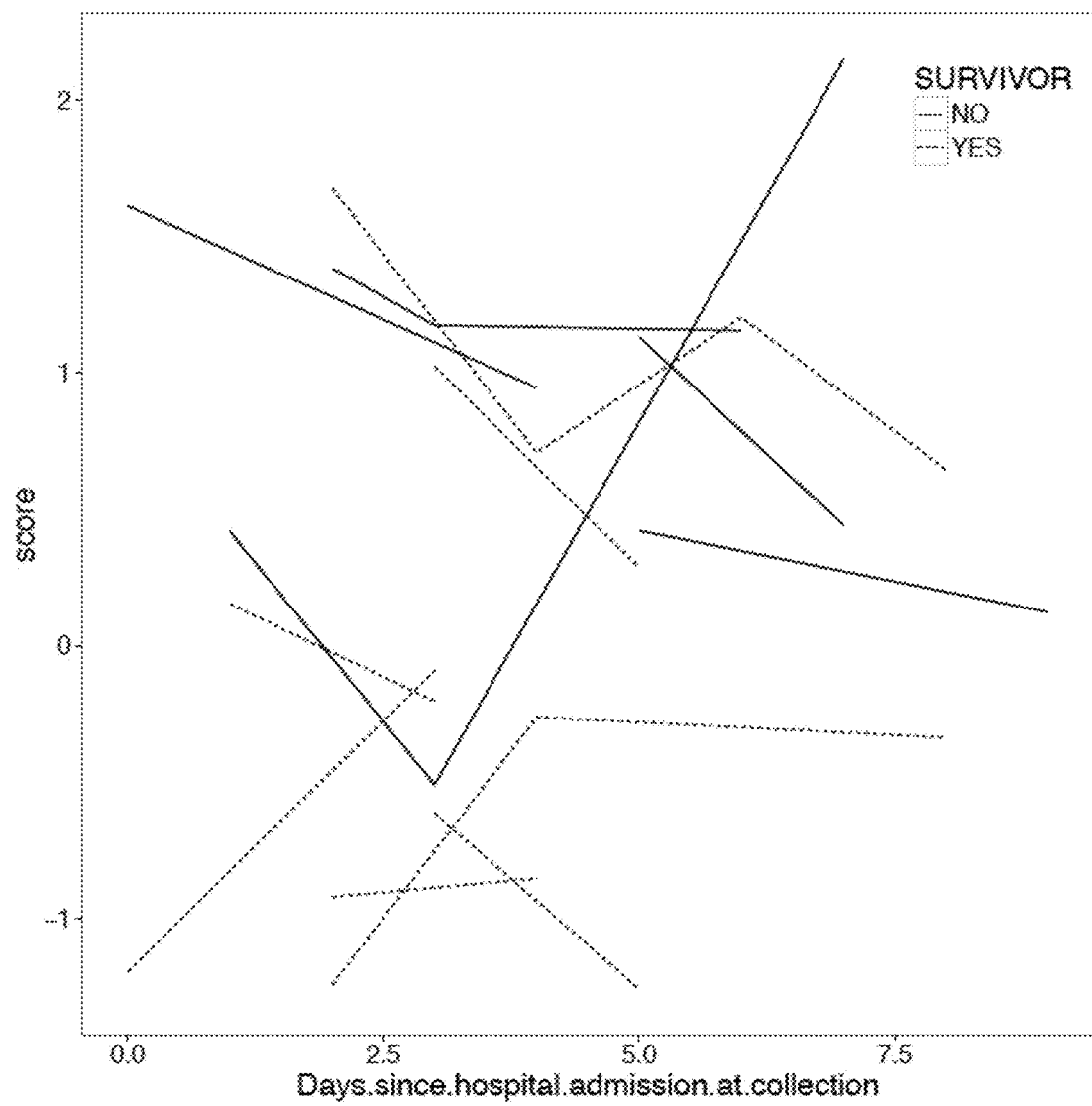
Figure 11A:
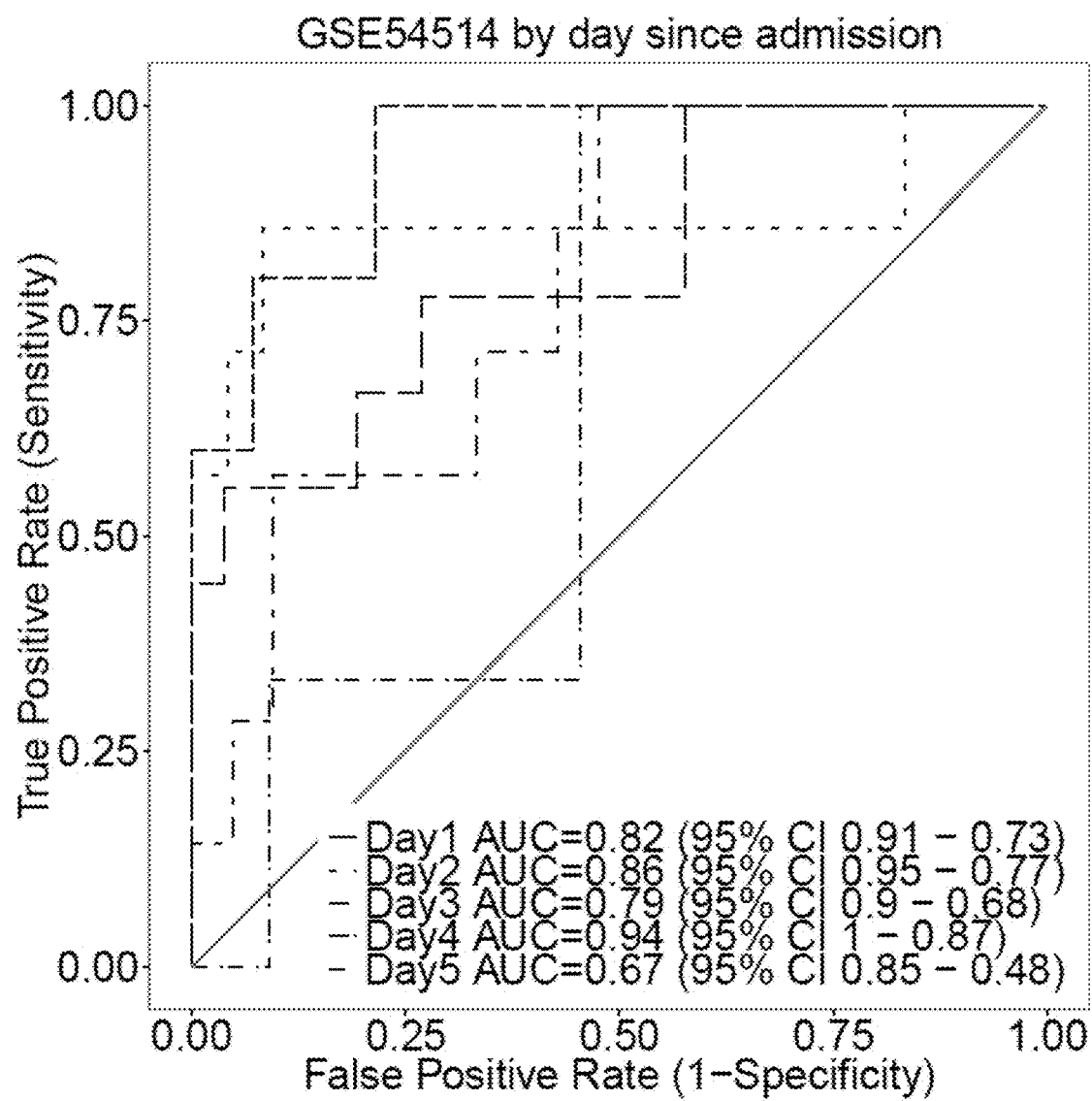
FIGS. 11A and 11B show longitudinal data from validation dataset GSE54514.
Figure 11B:
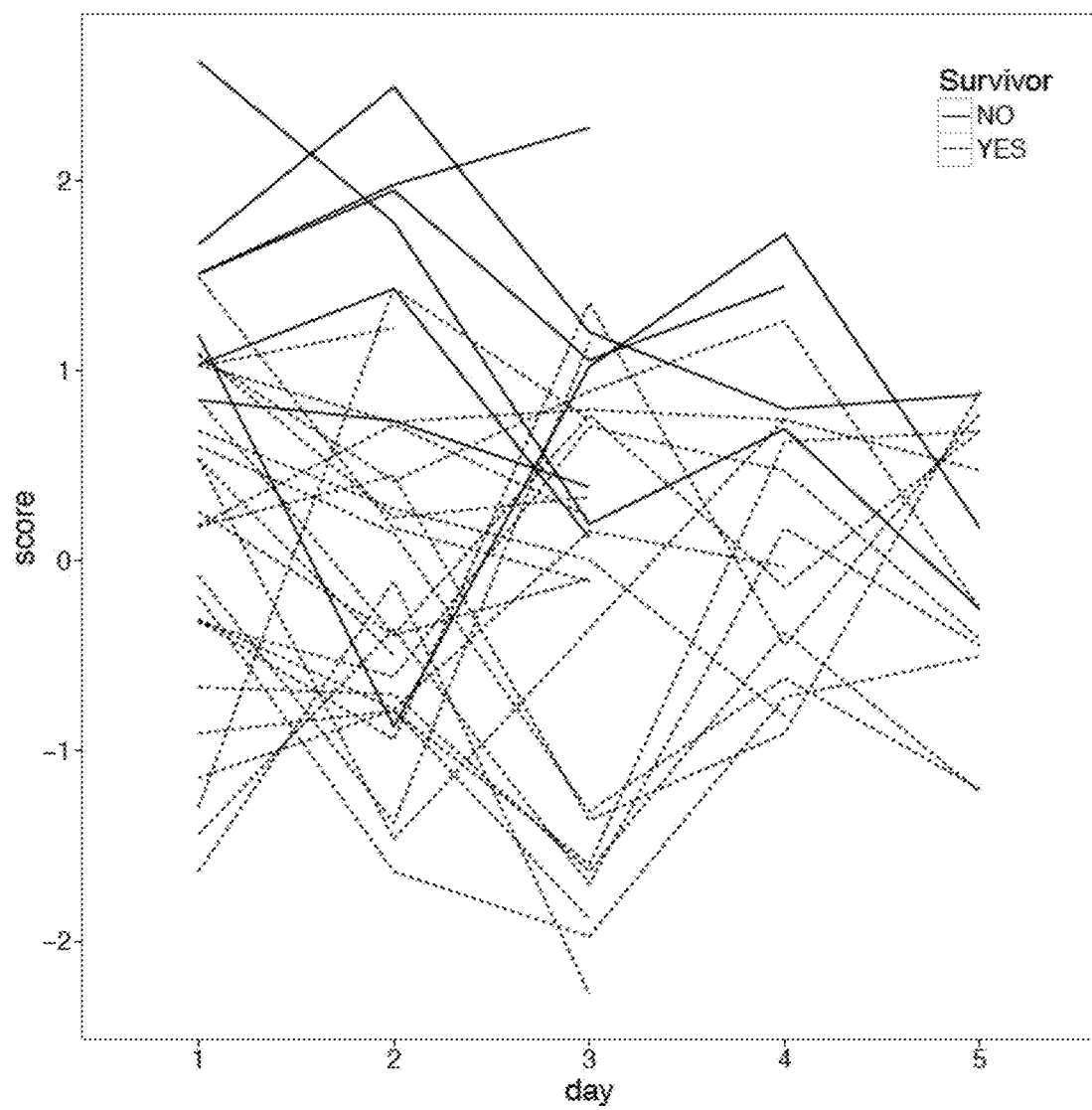

We next examined the prognostic power of the 12-gene score in the 5 validation datasets that examined sepsis patients at admission (Table 3). For the two cohorts which had longitudinal samples (GSE21802 and GSE54514), we examined only the first 48 or 24 hours after admission, respectively, without repeating any patients within the analysis. This thus yielded a total of 415 survivors and 136 non-survivors. Across these five cohorts, the 12-gene score showed a summary AUC of 0.84 (95% CI 0.58-0.96; FIGS. 7-9). Notably, the AUC was lowest in E-MTAB-4421.51; this cohort allowed patients to be enrolled in a window up to day 5 after admission, possibly biasing the results. In analysis of the two validation cohorts with longitudinal sampling (GSE21802, GSE54514), we saw similar trends, namely, a roughly preserved AUC over time, until survivor bias in the late time-points caused a drop in AUC (FIGS. 10-11). In addition, in both cohorts, the 12-gene score showed a general trend in decrease over time, meaning that a sample drawn at 5 days after sepsis diagnosis would have a lower expected score than a sample drawn at day 1. Such a finding may support a downward bias due to sampling technique in E-MTAB-4421.51. In addition, both GSE21802 and GSE54514 included admission severity scores; we again compared prognostic power alone and in combination with the 12-gene score, showing a small lift (0.02-0.05) in both cases.

Validation in the Glue Grant

Figure 12A:
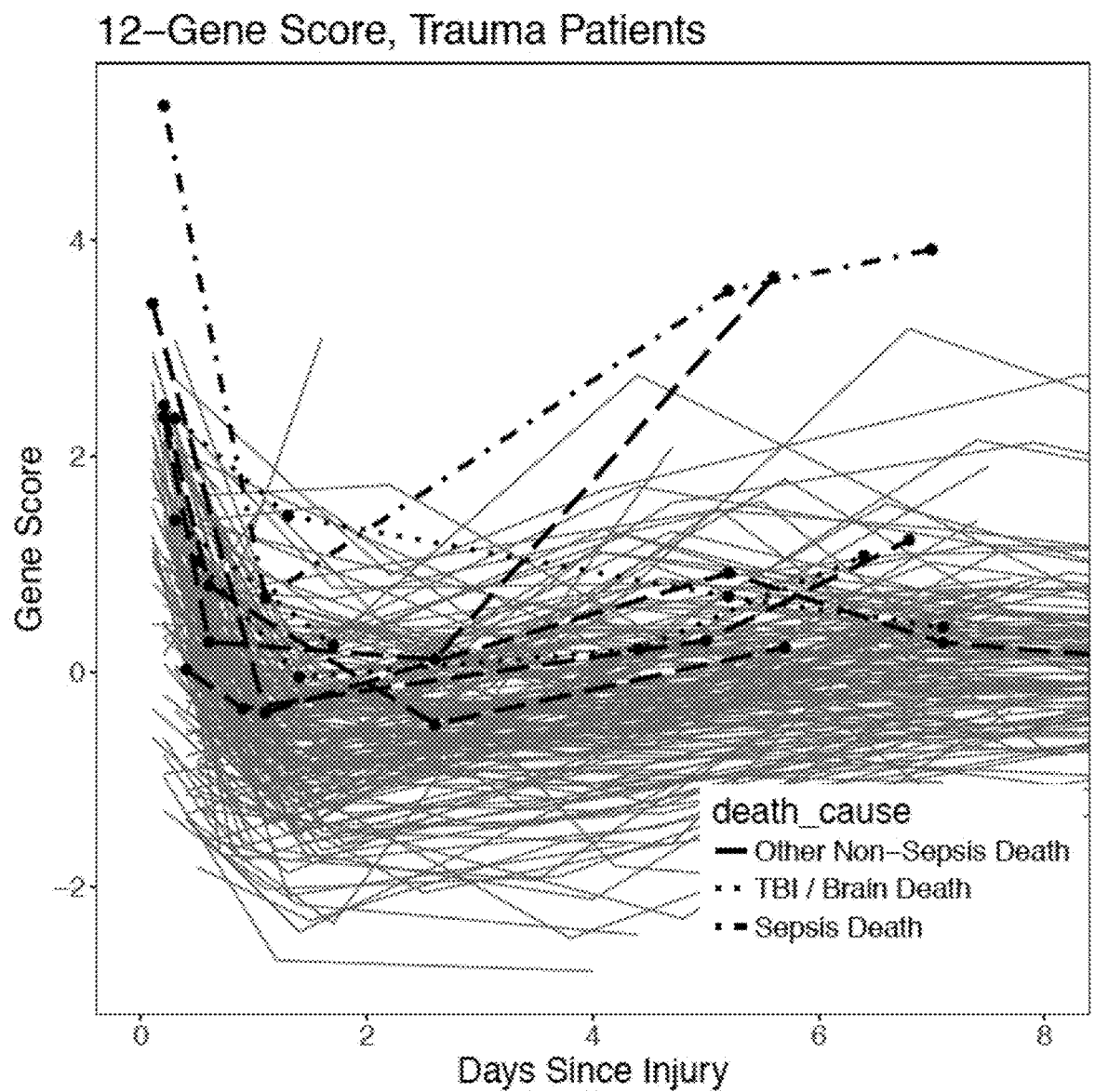
FIGS. 12A and 12B show longitudinal data from the Glue Grant trauma-buffy coat cohort.
Figure 12B:
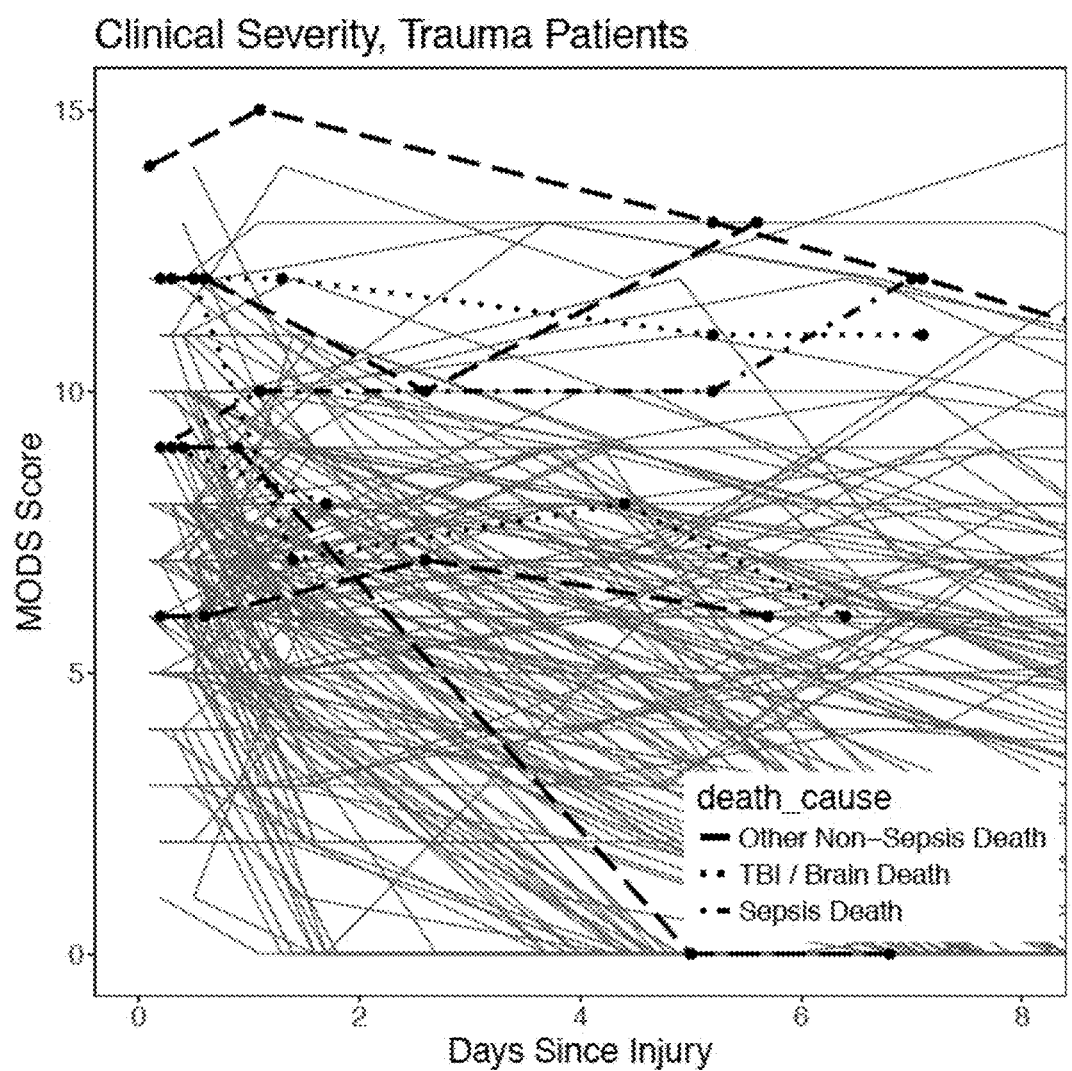
Figure 13A:
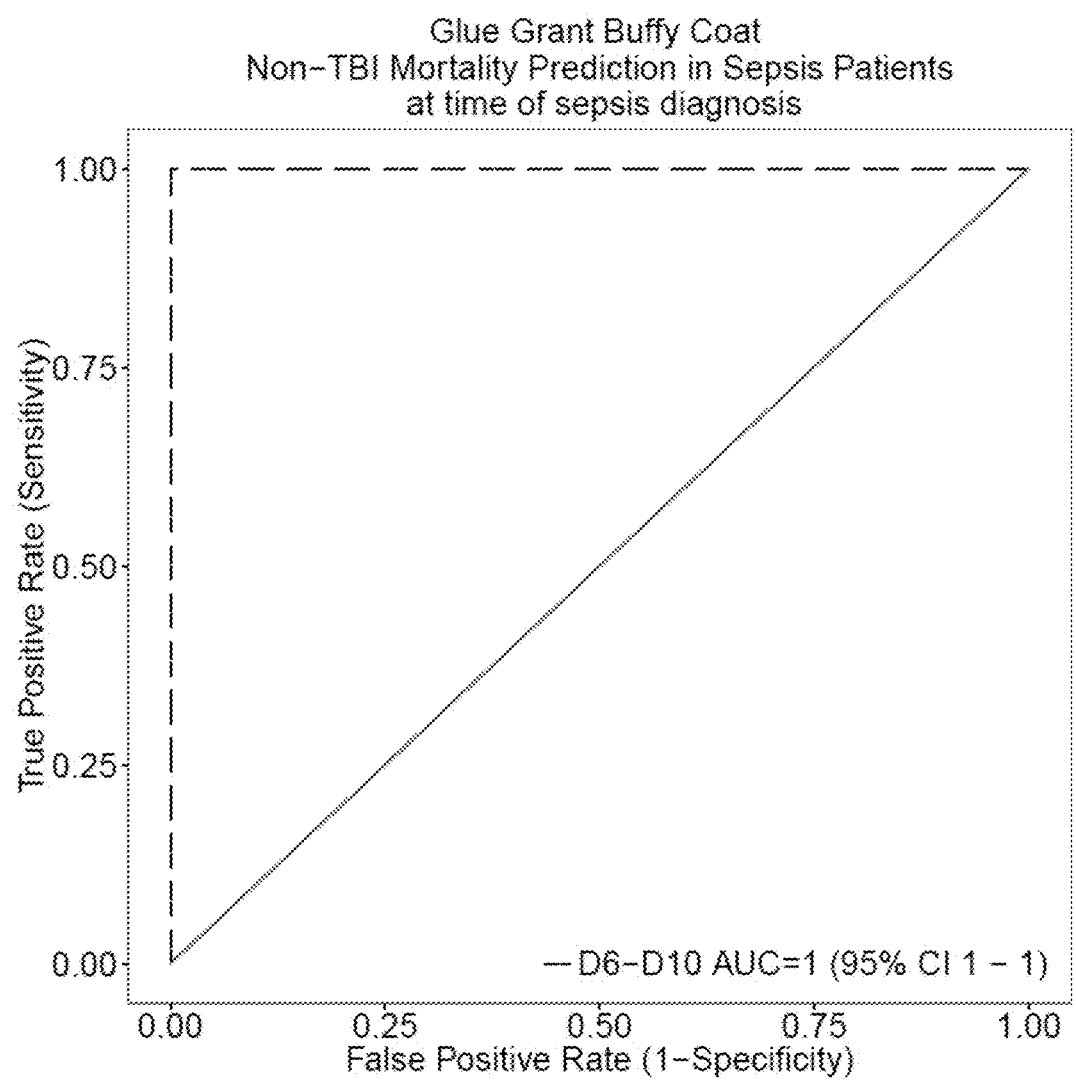
FIGS. 13A and 13B show ROC plots of mortality prediction broken into bins of time since admission in the Glue Grant trauma-buffy coat cohort.
Figure 13B:
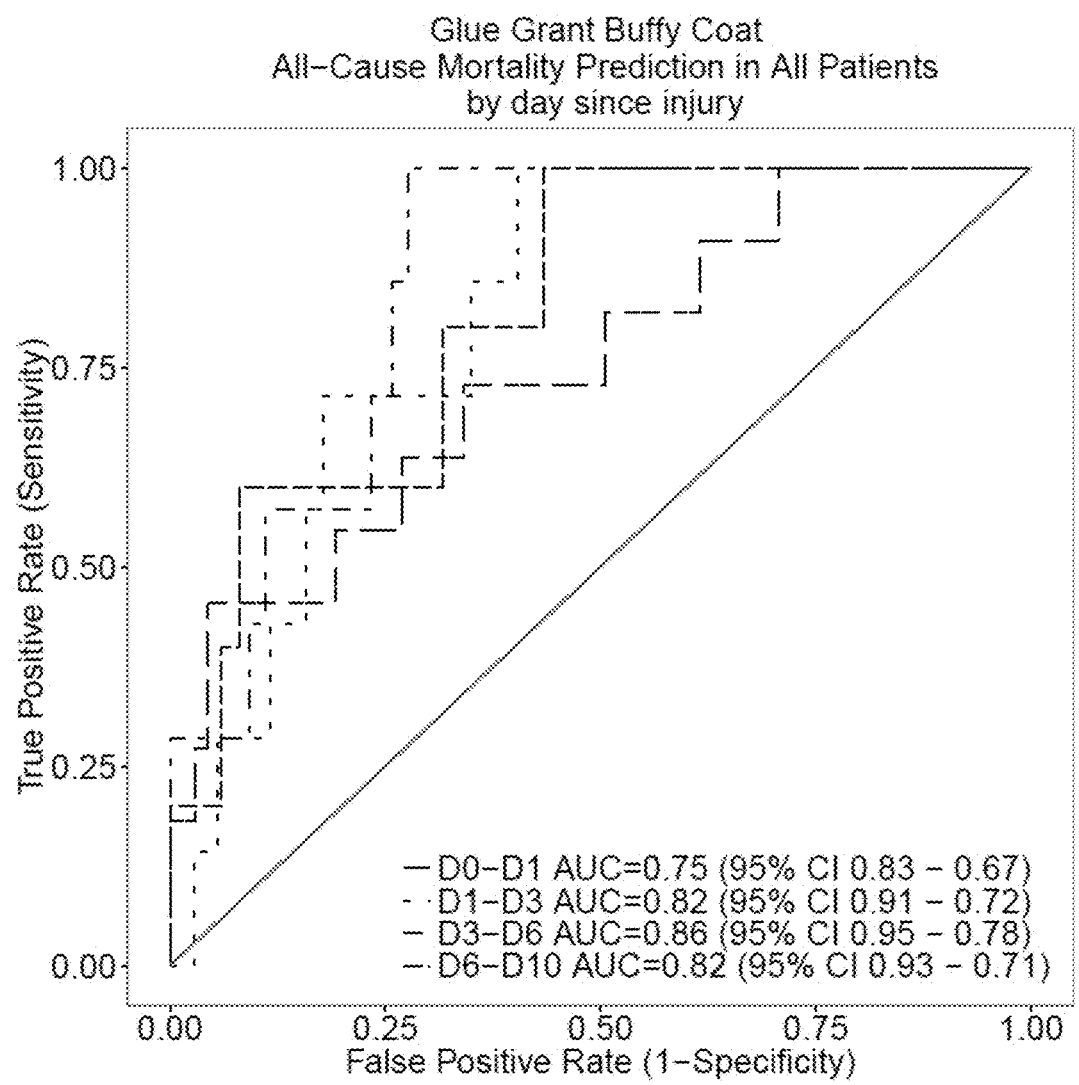
Figure 14A:
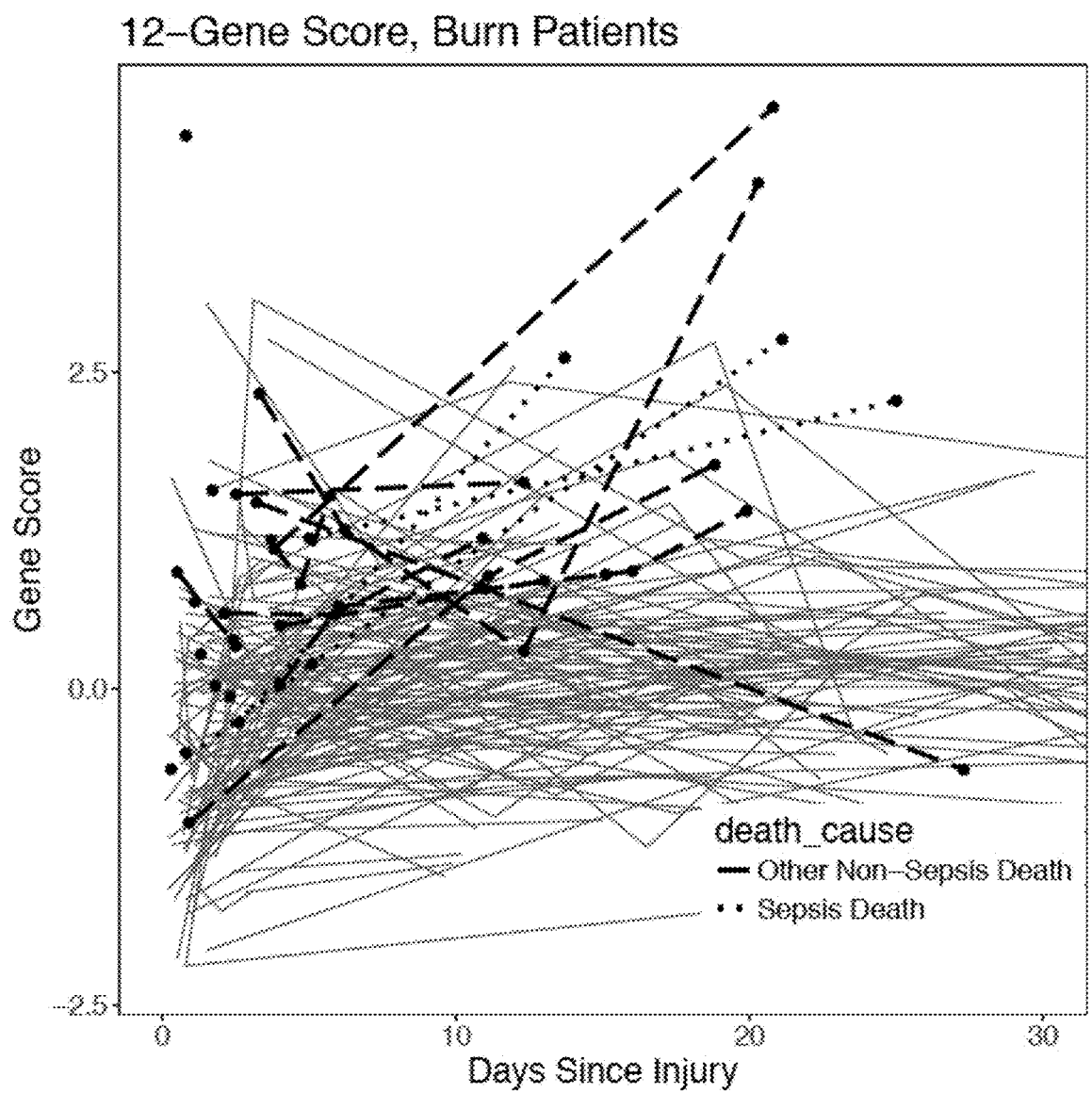
FIGS. 14A and 14B show longitudinal data from the Glue Grant burns-whole blood cohort.
Figure 14B:
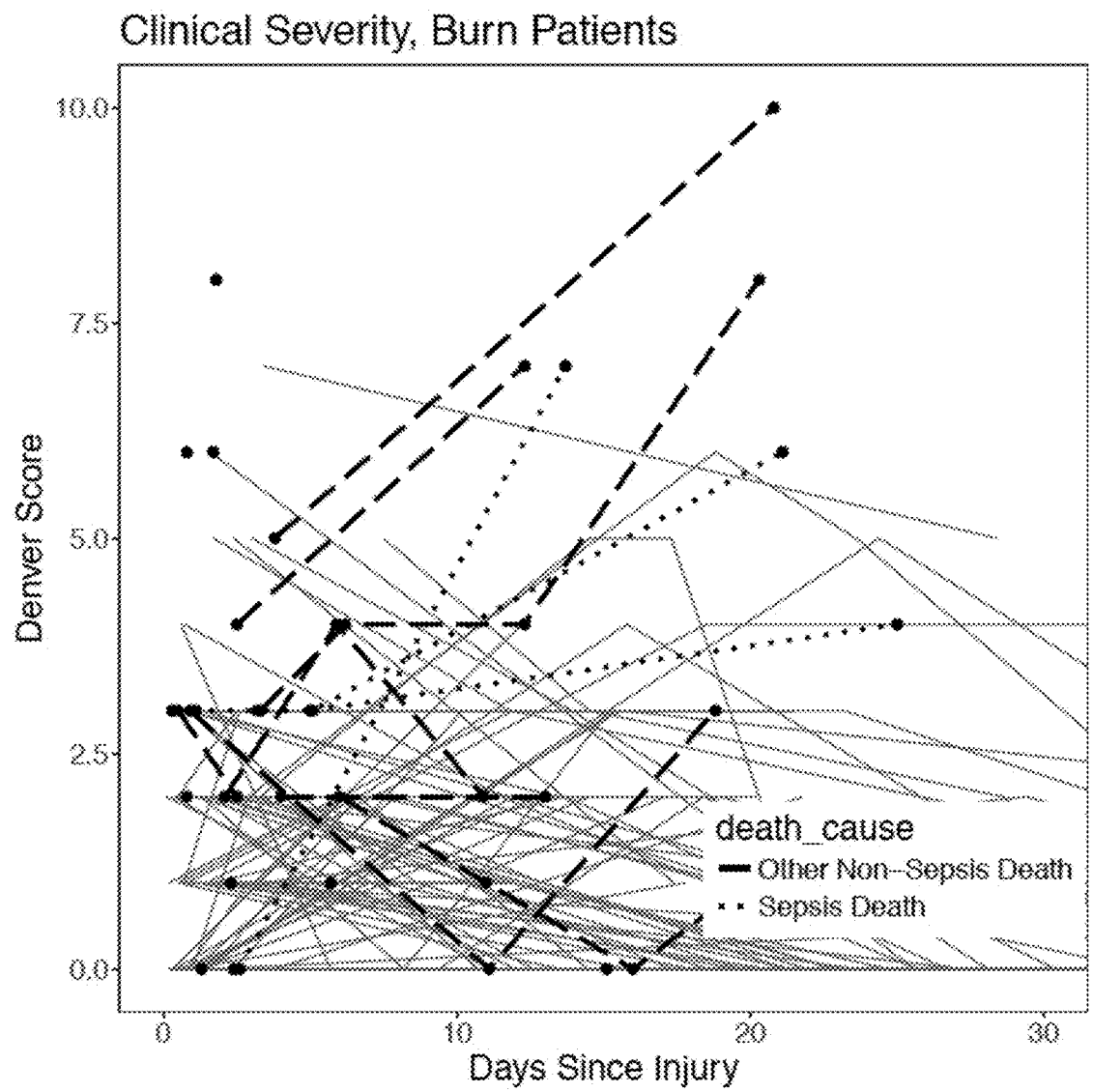
Figure 15A:
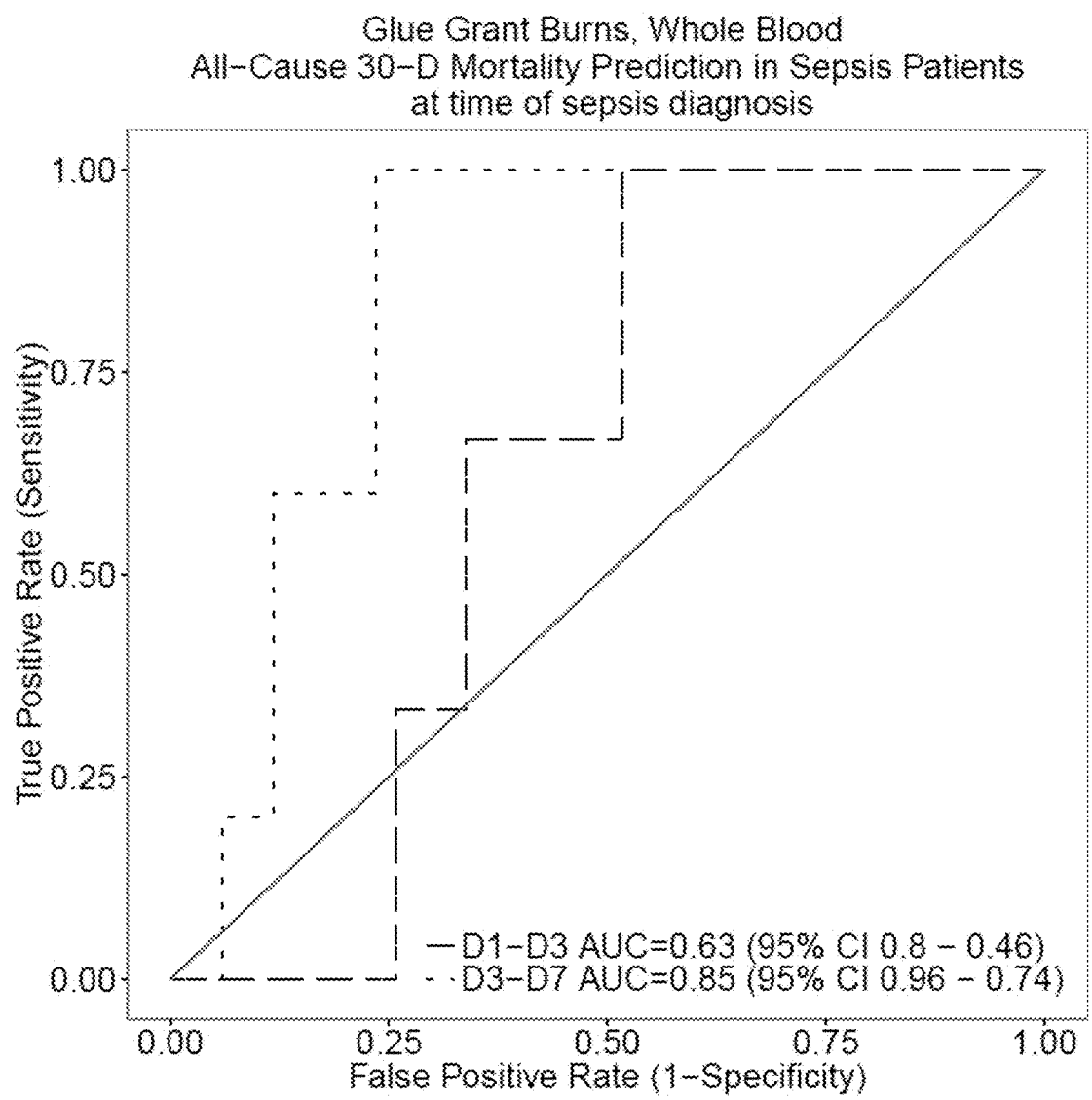
FIGS. 15A and 15B show ROC plots of mortality prediction broken into bins of time since admission in the Glue Grant burns-whole blood cohort.
Figure 15B:
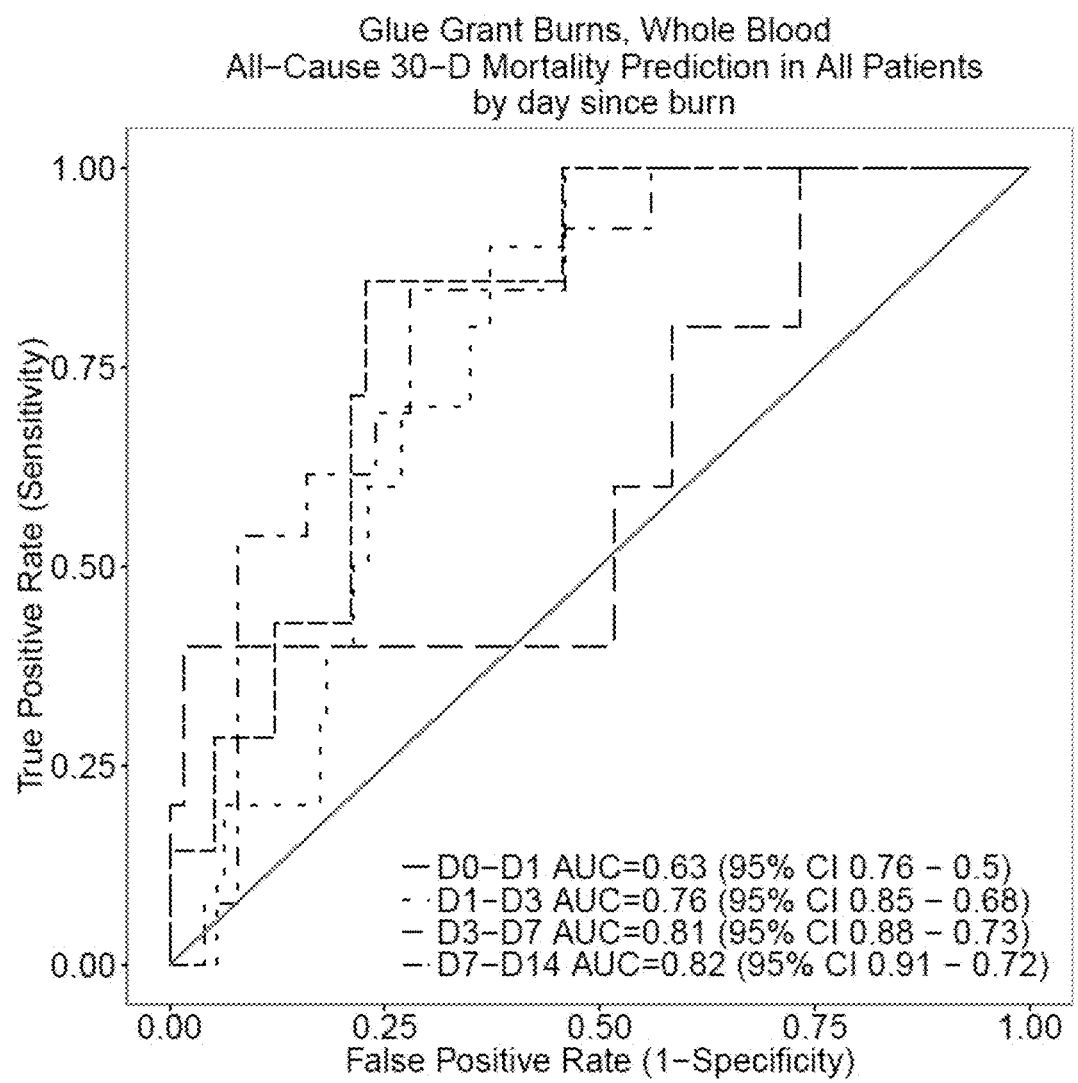

We next examined the Glue Grant trauma (buffy coat) and burns (whole blood) patients (Table 3). For the trauma cohorts, we first plotted trajectories of all patients for both 12-gene score and clinical severity score (FIG. 12), showing a clear trend of higher gene scores in the mortality cases. In the one defined sepsis death in this cohort, the patient's 12-gene scores are higher than all other scores at three of four timepoints. We also examined prognostic power using ROC curves, both for sepsis patients at time of diagnosis and for all patients over time since admission. The sepsis patients matched for time of diagnosis showed only one death, but this was perfectly predicted compared to the other 12 patients (FIG. 13A). The 12-gene score also showed moderate prognostic power for all-cause mortality among all patients over time (AUC 0.75-0.86, FIG. 13B). In the Glue Grant burns cohort, we performed the same type of analysis, with similar outcomes. Gene score trajectories of patients who died were generally separable from those who lived, though again clinical severity trajectories did a similarly good job of identifying these patients (FIG. 14). Examining time-matched patients with sepsis, predicting diagnosis, the 12-gene score had poor power at day 1-day 3 post-admission (AUC 0.63), but a much higher power at day 3-day 7 (AUC 0.85); these two time bins contained no overlapping patients (FIG. 15A). Examining the prediction of all-cause mortality longitudinally, the burns data showed a range of AUCs (0.63-0.82), showing an increased over time since admission, with particularly poor performance in the first 24 hours since burn (FIG. 15B).

Cell-Type-Specific Expression

Figure 16A:
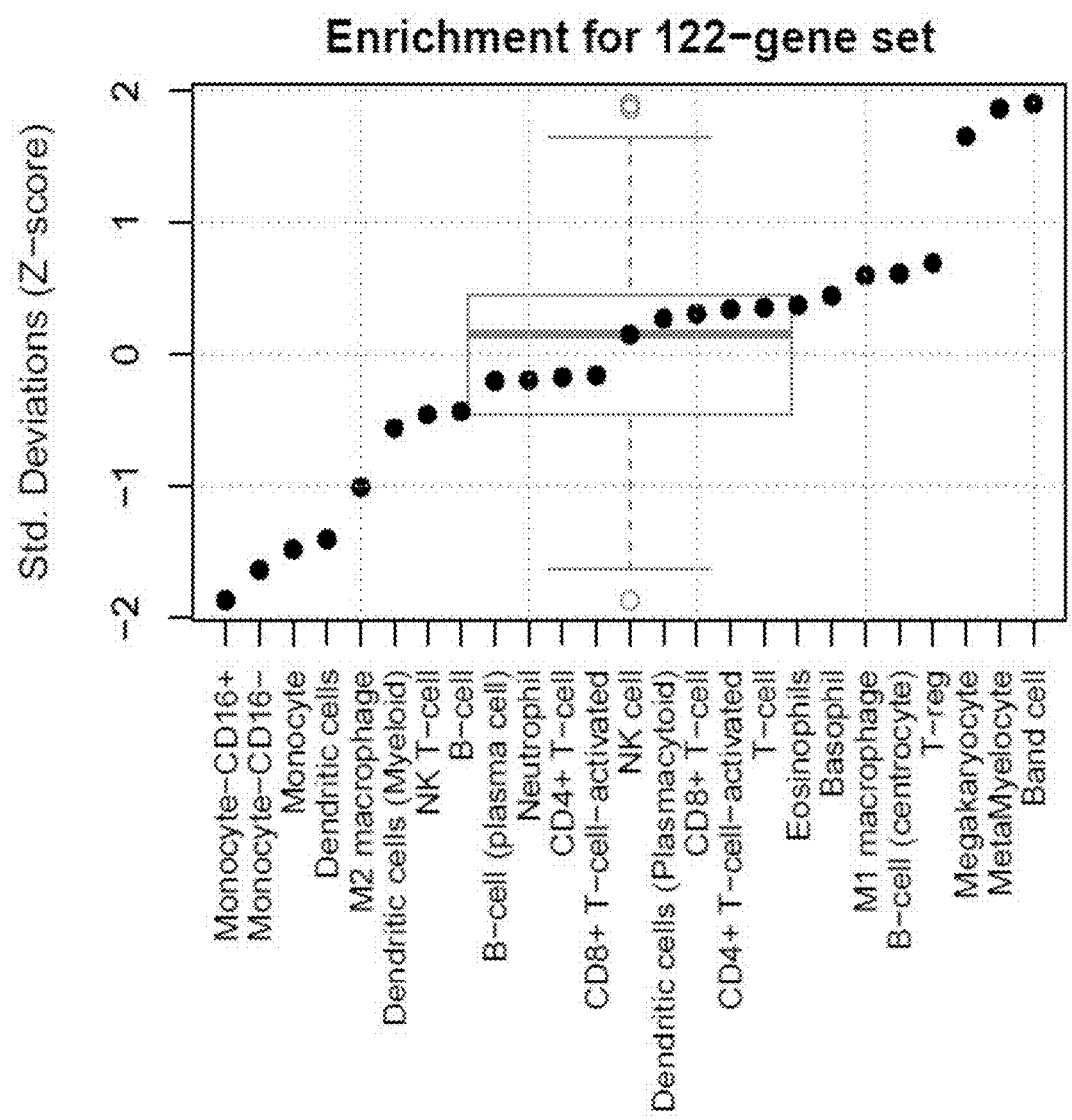
FIGS. 16A and 16B show cell-type enrichment plots of the 122-gene set (FIG. 16A) and the 12-gene set (FIG. 16B). Shown are Z-scores of the enrichment of each gene set across all sorted in vitro cell types shown.
Figure 16B:
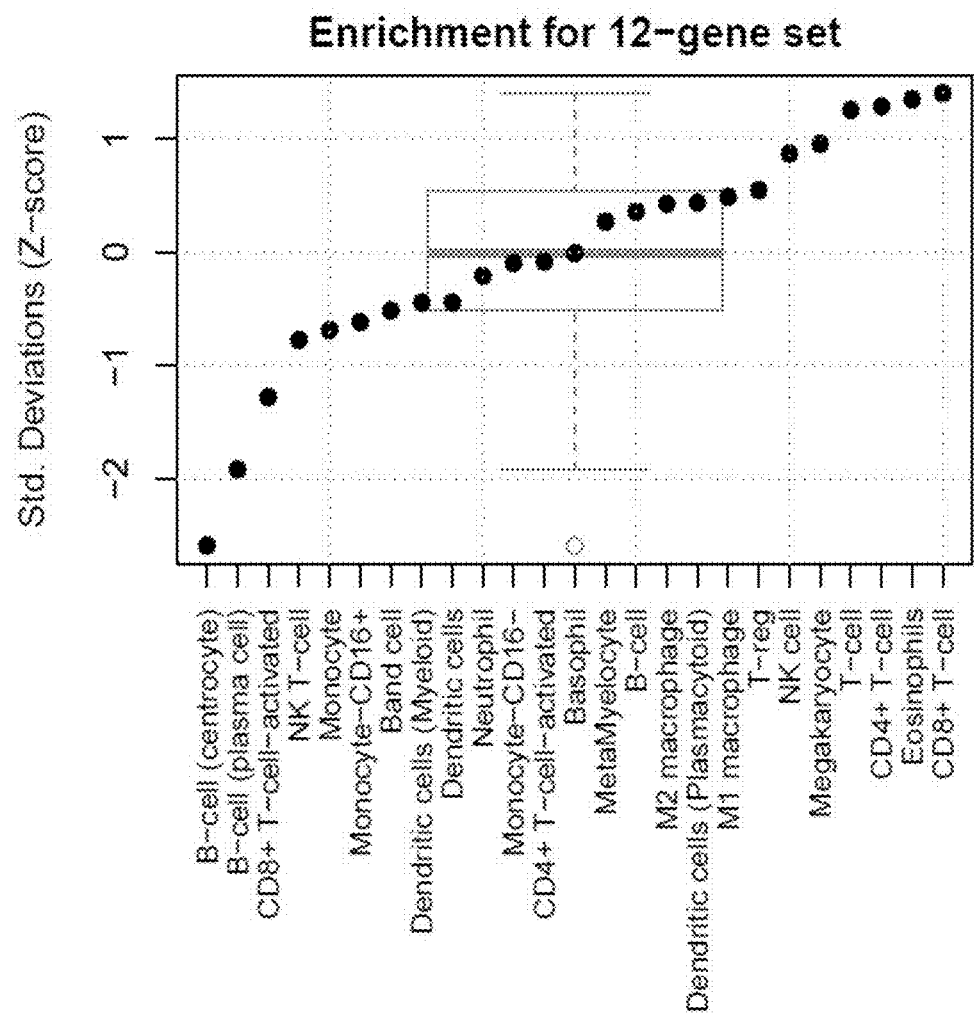

Finally, to gain some insight into the biology of these genes, we performed in silico cell-type expression analysis of both all 122 significant genes, as well as the prognostic 12-gene set, as previously described (FIG. 16). Here the hypothesis is that an increase in signal within a specific immune cell type may suggest that the change in expression of these genes in whole blood may in fact signal a detection of a cell-type shift, instead of (or in addition to) changes in intracellular transcript levels. Intriguingly, the 122-gene set showed significant enrichment in bands and metamyelocytes, indicating that immature neutrophils may be specifically linked to sepsis mortality, in line with some prior suggestions by other groups. However, the 12-gene set did not show any significant over-enrichment in any cell types. The negative signal found for centrocytes is unlikely to be biologically relevant, since these cell types are not present in the blood in meaningful quantities.

Discussion

Sepsis is an incredibly heterogeneous syndrome, including a wide possible range of patient conditions, comorbidities, acute severity, time since infections, and underlying immune states. Many have previously hypothesized that a molecular profile of the immune system may be able to predict sepsis outcomes. However, the best clinical tools for predicting outcomes remain blood lactate and clinical severity scores, both of which have several limitations. Here, we combined a large amount of data (12 cohorts, 650 patients) to define a set of just 12 genes that is able to predict mortality in septic patients. We validated this score directly in 5 cohorts with 551 patients, with a summary ROC AUC of 0.84. In addition, we showed in additional 421 patients admitted with severe trauma or burns that the 12-gene score has preserved predictive power for mortality in patients with sepsis, as well as some ability to predict all-cause mortality in very broad cohorts.

This molecular definition of the severity of the host response in sepsis is important for several reasons. First, better sepsis prognosis can improve clinical care by correctly matching patients with resources: sicker patients can be diverted to ICU with maximal intervention, while patients unlikely to die may be safely watched in the hospital ward. Second, both patients and clinicians can benefit from more-precise estimates of prognosis, allowing for better discussions of patient preferences and the choice to intervene. Finally, better molecular phenotyping of sepsis patients can allow for great improvements in clinical trials, through both (1) patient selection and prognostic enrichment for drugs and interventions, and (2) better assessments of observed-to-expected ratios for mortality[5,6].

The genes we have identified as being associated with sepsis mortality may also denote important underlying biology. For instance, the top three genes associated with mortality independent of clinical severity were azurophilic granule proteases, indicating a presence of very immature neutrophils (metamyelocytes) in the blood. Whether these proteases are themselves harmful, or are markers of harmful cell-type shifts, remains to be confirmed. Several groups have shown that late sepsis deaths are mostly due to an 'immune paralysis' that affects the adaptive immune system. The transcriptomic changes shown here may be thus part of a cascade of events that is indirectly associated with mortality through induction of adaptive immune collapse. These genes may thus be direct therapeutic targets, in addition to simply being markers for sepsis severity. More study is needed.

Our analysis has some weaknesses; most notably, the largest validation dataset, E-MTAB-4421.51 shows the worst performance of all datasets. There are at least three possible explanations for this: first, as described, this cohort allowed inclusion up to day five since admission, but did not include which day was associated with which patient in the public phenotype file. Since the score appears to fall over time in patients admitted with sepsis, and since there may be a bias towards sicker patients being enrolled later (as it is often difficult to enroll patients who are very sick at admission), this could lead to a downward bias. Second, it is possible that this cohort is 'sicker' than the other cohorts, although the mean APACHE scores of 18-23 are nearly identical to those of, say GSE54514, in which our diagnostic power was confirmed. Finally, of course it is possible that the gene set may simply not perform well in this cohort either due to its size or some other clinical factors that are unknown. This seems less likely given that in the 16 other discovery and validation cohorts, the lowest AUC is 0.72 (GSE10474, N=33). In any case, further prospective confirmation is necessary prior to clinical application.

Overall, through integrated analysis of the available transcriptomic data in sepsis, we have derived a set of 12 genes whose levels can be used to predict short-term (30-day) mortality in sepsis patients, with confirmation across 551 independent patients from 5 cohorts. These findings indicate that the whole blood transcriptome does carry an early signal for eventual mortality. They also illustrate a set of targets for further mechanistic or therapeutic study in severe sepsis. Finally, the 12-gene set could potentially be used directly as a prognostic test, though further prospective confirmation is necessary.

REFERENCES

1. Singer M, Deutschman C S, Seymour C W, et al. The Third International Consensus Definitions for Sepsis and Septic Shock (Sepsis-3). *JAMA*. February 2016; 315(8): 801-810.
2. Torio C A, Andrews R A. National Inpatient Hospital Costs: The Most Expensive Conditions by Payer, 2011. HCUP Statistical Brief #160. Rockville, Md.: Agency for Healthcare Research and Quality; August 2013.

3. Liu V, Escobar G J, Greene J D, et al. Hospital Deaths in Patients With Sepsis From 2 Independent Cohorts. *JAMA*. May 2014.
4. Kaukonen K M, Bailey M, Pilcher D, Cooper D J, Bellomo R. Systemic inflammatory response syndrome criteria in defining severe sepsis. *N Engl J Med*. April 2015; 372(17):1629-1638.
5. Opal S M, Dellinger R P, Vincent J L, Masur H, Angus D C. The next generation of sepsis clinical trial designs: what is next after the demise of recombinant human activated protein C?*. *Crit Care Med*. July 2014; 42(7): 1714-1721.
6. Cohen J, Vincent J L, Adhikari N K, et al. Sepsis: a roadmap for future research. *Lancet Infect Dis*. May 2015; 15(5):581-614.
7. Sweeney T E, Wong H R. Risk stratification and prognosis in sepsis: what have we learned from microarrays? *Clinics in Chest Medicine*. Accepted, 2015.
8. Parnell G, McLean A, Booth D, Huang S, Nalos M, Tang B. Aberrant cell cycle and apoptotic changes characterise severe influenza A infection—a meta-analysis of genomic signatures in circulating leukocytes. *PLoS One*. 2011; 6(3):e17186.
9. Parnell G P, Tang B M, Nalos M, et al. Identifying key regulatory genes in the whole blood of septic patients to monitor underlying immune dysfunctions. *Shock*. September 2013; 40(3):166-174.
10. Wong H R, Shanley T P, Sakthivel B, et al. Genome-level expression profiles in pediatric septic shock indicate a role for altered zinc homeostasis in poor outcome. *Physiol Genomics*. July 2007; 30(2):146-155.
11. Tsalik E L, Langley R J, Dinwiddie D L, et al. An integrated transcriptome and expressed variant analysis of sepsis survival and death. *Genome Med*. 2014; 6(11):111.
12. Almansa R, Heredia-Rodríguez M, Gomez-Sanchez E, et al. Transcriptomic correlates of organ failure extent in sepsis. *J Infect*. May 2015; 70(5):445-456.
13. Wong H R, Cvijanovich N Z, Anas N, et al. Developing a clinically feasible personalized medicine approach to pediatric septic shock. *Am J Respir Crit Care Med*. February 2015; 191(3):309-315.
14. Davenport E E, Burnham K L, Radhakrishnan J, et al. Genomic landscape of the individual host response and outcomes in sepsis: a prospective cohort study. *Lancet Respir Med*. February 2016.
15. Sweeney T E, Shidham A, Wong H R, Khatri P. A comprehensive time-course-based multicohort analysis of sepsis and sterile inflammation reveals a robust diagnostic gene set. *Sci Transl Med*. May 2015; 7(287):287ra71.
16. Khatri P, Roedder S, Kimura N, et al. A common rejection module (CRM) for acute rejection across multiple organs identifies novel therapeutics for organ transplantation. *J Exp Med*. October 2013; 210(11):2205-2221.
17. Andres-Terre M, McGuire H M, Pouliot Y, et al. Integrated, Multi-cohort Analysis Identifies Conserved Transcriptional Signatures across Multiple Respiratory Viruses. *Immunity*. December 2015; 43(6):1199-1211.
18. Sweeney T E, Braviak L, Tato C M, Khatri P. Genome-wide expression for diagnosis of pulmonary tuberculosis: a multicohort analysis. *Lancet Respir Med*. March 2016; 4(3):213-224.
19. Howrylak J A, Dolinay T, Lucht L, et al. Discovery of the gene signature for acute lung injury in patients with sepsis. *Physiol Genomics*. April 2009; 37(2):133-139.
20. Bermejo-Martin J F, Martin-Loeches I, Rello J, et al. Host adaptive immunity deficiency in severe pandemic influenza. *Crit Care*. 2010; 14(5):R167.
21. Dolinay T, Kim Y S, Howrylak J, et al. Inflammasome-regulated cytokines are critical mediators of acute lung injury. *Am J Respir Crit Care Med*. June 2012; 185(11): 1225-1234.
22. Ahn S H, Tsalik E L, Cyr D D, et al. Gene expression-based classifiers identify Staphylococcus aureus infection in mice and humans. *PLoS One*. 2013; 8(1):e48979.
23. Tsalik E L, Henao R, Nichols M, et al. Host gene expression classifiers diagnose acute respiratory illness etiology. *Sci Transl Med*. January 2016; 8(322):322ra311.
24. Wong H R, Cvijanovich N, Allen G L, et al. Genomic expression profiling across the pediatric systemic inflammatory response syndrome, sepsis, and septic shock spectrum. *Crit Care Med*. May 2009; 37(5):1558-1566.
25. Wong H R, Cvijanovich N, Lin R, et al. Identification of pediatric septic shock subclasses based on genome-wide expression profiling. *BMC Med*. 2009; 7:34.
26. Kangelaris K N, Prakash A, Liu K D, et al. Increased expression of neutrophil-related genes in patients with early sepsis-induced ARDS. *Am J Physiol Lung Cell Mol Physiol*. June 2015; 308(11):L1102-1113.
27. Seok J, Warren H S, Cuenca A G, et al. Genomic responses in mouse models poorly mimic human inflammatory diseases. *Proc Natl Acad Sci USA*. February 2013; 110(9):3507-3512.
28. Warren H S, Elson C M, Hayden D L, et al. A genomic score prognostic of outcome in trauma patients. *Mol Med*. 2009 July-August 2009; 15(7-8):220-227.
29. Xiao W, Mindrinos M N, Seok J, et al. A genomic storm in critically injured humans. *J Exp Med*. December 2011; 208(13):2581-2590.
30. Desai K H, Tan C S, Leek J T, et al. Dissecting inflammatory complications in critically injured patients by within-patient gene expression changes: a longitudinal clinical genomics study. *PLoS Med*. September 2011; 8(9):e1001093.
31. Chen H, Manning A, Dupuis J. A Method of Moments Estimator for Random Effect Multivariate Meta-Analysis. *Biometrics*. December 2012 2012; 68(4):1278-1284.
32. Becker B, Wu M. The synthesis of regression slopes in meta-analysis. *Statistical Science*. August 2007 2007; 22(3):414-429.
33. Kester A D, Buntinx F. Meta-analysis of ROC curves. *Med Decis Making*. 2000 October-December 2000; 20(4): 430-439.
34. Irwin A D, Marriage F, Mankhambo L A, et al. Novel biomarker combination improves the diagnosis of serious bacterial infections in Malawian children. *BMC Med Genomics*. 2012; 5:13.
35. Kwan A, Hubank M, Rashid A, Klein N, Peters M J. Transcriptional instability during evolving sepsis may limit biomarker based risk stratification. *PLoS One*. 2013; 8(3):e60501.
36. Pankla R, Buddhisa S, Berry M, et al. Genomic transcriptional profiling identifies a candidate blood biomarker signature for the diagnosis of septicemic melioidosis. *Genome Biol*. 2009; 10(11):R127.
37. Berdal J E, Mollnes T E, Wehre T, et al. Excessive innate immune response and mutant D222G/N in severe A (H1N1) pandemic influenza. *J Infect*. October 2011; 63(4):308-316.
38. Lill M, Kõks S, Soomets U, et al. Peripheral blood RNA gene expression profiling in patients with bacterial meningitis. *Front Neurosci*. 2013; 7:33.

While the preferred embodiments of the invention have been illustrated and described, it will be appreciated that various changes can be made therein without departing from the spirit and scope of the invention.

What is claimed is:

1. A method of administering urgent care to a patient, comprising:
    (a) identifying the patient as having a high risk of mortality within 30 days, wherein the patient has increased levels of expression of the DEFA4, CD163, PER1, RGS1, HIF1A, SEPP1, C11orf74, and CIT biomarkers and decreased levels of expression of the LY86, TST, and KCNJ2 biomarkers compared to reference value ranges; and
    (b) administering an antimicrobial therapy to the patient, administering an immunomodulating therapy to the patient, or administering an organ-specific treatment to the patient.

2. The method of claim 1, wherein step (b) comprises administering an antimicrobial therapy to the patient.

3. The method of claim 1, wherein step (b) comprises administering an immunomodulating therapy to the patients.

4. The method of claim 1, wherein step (b) comprises administering an organ-specific treatment to the patient.

5. The method of claim 4, wherein the organ-specific treatment comprises one or more of connecting the patient to any one or more of a mechanical ventilator, a pacemaker, a defibrillator, a dialysis or renal replacement therapy machine, an invasive monitor including a pulmonary artery catheter, arterial blood pressure catheter, or central venous pressure catheter, or administering blood products, vasopressors, or sedatives.

6. The method of claim 1, wherein the patient has increased levels of expression of the DEFA4, CD163, PER1, RGS1, HIF1A, SEPP1, C11orf74, and CIT biomarkers and decreased levels of expression of the LY86, TST, and KCNJ2 biomarkers in blood, buffy coat, band cells, or metamyelocytes compared to reference value ranges.

7. The method of claim 1, wherein the levels of the biomarkers are compared to time-matched reference values for infected or non-infected subjects.

8. The method of claim 1, wherein the biomarkers are protein biomarkers.

9. The method of claim 1, wherein the biomarkers are RNA biomarkers.

10. The method of claim 1, further comprising admitting the patient to an intensive care unit.

11. The method of claim 1, wherein the patient has sepsis, trauma or a burn.

* * * * *